US009512479B2

(12) United States Patent
Kurnool et al.

(10) Patent No.: US 9,512,479 B2
(45) Date of Patent: Dec. 6, 2016

(54) METHODS FOR SAMPLE TRACKING

(75) Inventors: Purnima Kurnool, Bangalore (IN); Betty Bei Yue Wu, Beijing (CN); Peter M. Banks, Santa Rosa, CA (US)

(73) Assignee: HandyLab, Inc., Franklin Lakes, NJ (US)

( * ) Notice: Subject to any disclaimer, the term of this patent is extended or adjusted under 35 U.S.C. 154(b) by 0 days.

(21) Appl. No.: 12/326,040

(22) Filed: Dec. 1, 2008

(65) Prior Publication Data

US 2009/0298049 A1 Dec. 3, 2009

Related U.S. Application Data

(63) Continuation of application No. 10/360,854, filed on Feb. 10, 2003, now abandoned.

(51) Int. Cl.
C12Q 1/68 (2006.01)

(52) U.S. Cl.
CPC ....... C12Q 1/6876 (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 5,143,854 A | 9/1992 | Pirrung et al. | |
| 5,364,759 A | 11/1994 | Caskey et al. | |
| 5,445,934 A | 8/1995 | Fodor et al. | |
| 5,459,039 A | 10/1995 | Modrich et al. | |
| 5,498,531 A | 3/1996 | Jarrell | |
| 5,561,071 A | 10/1996 | Hollenberg et al. | |
| 5,571,639 A | 11/1996 | Hubbell et al. | |
| 5,576,180 A * | 11/1996 | Melançon et al. | 435/6.16 |
| 5,585,069 A * | 12/1996 | Zanzucchi et al. | 422/505 |
| 5,593,839 A | 1/1997 | Hubbell et al. | |
| 5,599,668 A | 2/1997 | Stimpson et al. | |
| 5,605,662 A | 2/1997 | Heller et al. | |
| 5,632,957 A | 5/1997 | Heller et al. | |
| 5,671,303 A | 9/1997 | Shieh et al. | |
| 5,728,532 A | 3/1998 | Ackley | |
| 5,731,152 A | 3/1998 | Maracas et al. | |
| 5,733,509 A | 3/1998 | Ackley et al. | |
| 5,733,729 A | 3/1998 | Lipshutz et al. | |
| 5,741,644 A | 4/1998 | Kambara et al. | |
| 5,741,645 A | 4/1998 | Orr et al. | |
| 5,763,599 A | 6/1998 | Pfleiderer et al. | |
| 5,795,716 A | 8/1998 | Chee et al. | |
| 5,821,060 A | 10/1998 | Arlinghaus et al. | |
| 5,827,482 A | 10/1998 | Shieh et al. | |
| 5,888,736 A * | 3/1999 | Lacroix et al. | 435/6.12 |
| 6,060,243 A | 5/2000 | Tang et al. | |
| 6,575,188 B2 | 6/2003 | Parunak | |
| 7,157,228 B2 * | 1/2007 | Hashmi et al. | 435/6.16 |
| 2002/0142482 A1 | 10/2002 | Wu et al. | |
| 2002/0143437 A1 | 10/2002 | Handique et al. | |
| 2003/0085274 A1 * | 5/2003 | Leaton et al. | 235/380 |
| 2004/0188526 A1 | 9/2004 | Olsson et al. | |
| 2008/0226553 A1 * | 9/2008 | Lowe et al. | 424/9.1 |

FOREIGN PATENT DOCUMENTS

| | | |
|---|---|---|
| WO | WO 92/10092 | 6/1992 |
| WO | WO 94/16101 | 7/1994 |
| WO | WO 03052101 A1 | 6/2003 |

OTHER PUBLICATIONS

Ferrie et al. (Am J Hum Genet, 1992, 51:251-262, IDS reference).*
Brummelkamp et al. (Nature Reviews Cancer, 2003, vol. 3, p. 781-789).*
Winzeler et al. (Science, 1999, 285:901-906).*
Itakura et al. (Int J Inf Secur, 2002, 1:149-160).*
Corach et al. (Electrophoresis, 1995, 16, p. 1617-1623).*
Amos, et al., "Testing Environment for Single-Gene Disorders in U.S. Reference Laboratories," Human Mutation, 1998, vol. 12, pp. 293-300.
Botstein, D. et al., "Construction of a Genetic Linkage Map in man Using Restriction Fragment Length Polymorphisms", *Am. J. Hum. Genet.*, vol. 32 (1980), pp. 314-331.
Fauser, S. et al., "Simultaneous detection of multiple point mutations using fluorescence-coupled competitive primer extension", *Biotechniques*, vol. 22, No. 5 (May 1997), pp. 964-968.
Fischer, S.G. et al., "DNA fragments differing by single base-pair substitutions are separated in denaturing gradient gels: Correspondence with melting theory", *Proc. Nat. Acad. Sci. USA*, vol. 80 (1983), pp. 1579-1583.
Fox, S.A. et al., "Rapid genotyping of hepatitis C virus isolates by dideoxy fingerprinting", *Journal of Virological Methods*, vol. 53 (1995), pp. 1-9.
Gibbs, R.A. et al., "Detection of single DNA base differences by competitive oligonucleotide priming", *Nucleic Acids Research*, vol. 17, No. 7 (1989), pp. 2437-2448.
Griffin, H.G. et al., "DNA sequencing: Recent innovations and future trends", *Applied Biochemistry and Biotechnology*, vol. 38(1993), pp. 147-159.
Haff, L.A. et al., "Single-Nucleotide Polymorphism Identification Assays Using a Thermostable DNA Polymerase and Delayed Extraction MALDI-TOF Mass Spectrometry", *Genome Research*, vol. 7 (1997), pp. 378-388; downloaded on Mar. 5, 2007.

(Continued)

*Primary Examiner* — Stephanie K Mummert
(74) *Attorney, Agent, or Firm* — Knobbe, Martens, Olson & Bear, LLP

(57) ABSTRACT

A method and apparatus are provided for identifying a biological sample obtained during either paternity screening, genetic screening, prenatal diagnosis, presymptomatic diagnosis, diagnosis to detect the presence of a target microorganism carrier detection analysis, forensic chemical analysis, or diagnosis of a subject to determine whether a subject is afflicted with a particular disease or disorder, or is at risk of developing a particular disorder, wherein the result obtained from the analysis is associated with the unique DNA fingerprint biological barcode of the genotype of the subject being analyzed. The methods and apparatus of the invention have application in the fields of diagnostic medicine, disease diagnosis in animals and plants, identification of genetically inherited diseases in humans, family relationship analysis, forensic analysis, and microbial typing.

33 Claims, 9 Drawing Sheets

(56) References Cited

OTHER PUBLICATIONS

Jeffreys, A.J. et al., "Individual-specific 'fingerprints' of human DNA", *Nature*, vol. 316 (Jul. 4, 1985), pp. 76-79.
Lee, L.G. et al., "Allelic discrimination by nick-translation PCR with fluorogenic probes", *Nucleic Acids Research*, vol. 21, No. 16 (1993), pp. 3761-3766.
Livache, et al., "Polypyrrole DNA Chip on a Silicon Device: Example of Hepatitis C Virus Genotyping," Analytical Biochemistry, 1998, vol. 255, pp. 188-194.
Newton, C.R. et al., "Analysis of any point mutation in DNA. The amplification refractory mutation system (ARMS)", *Nucleic Acids Research*, vol. 17, No. 7 (1989), pp. 2503-2516.
Nikiforov, T.T. et al., "Genetic Bit Analysis: a solid phase method for typing single nucleotide polymorphisms", *Nucleic Acids Research*, vol. 22, No. 20 (1994), pp. 4167-4175.
Olson, M. et al., "A Common Language for Physical Mapping of the Human Genome", *Science*, vol. 245 (1989), pp. 1434-1435; downloaded on Mar. 5, 2007.
Orita, M. et al., "Rapid and Sensitive Detection of Point Mutations and DNA Polymorphisms Using the Polymerase Chain Reaction", *Genomics*, vol. 5 (1989), pp. 874-879.
Sheldon, E.L. et al., "Matrix DNA Hybridization", *Clinical Chemistry*, vol. 39, No. 4 (1993), pp. 718-719.
Smith, "Hepatitis C Virus," BMJ, 1995 vol. 310, pp. 1-2 (print out).
Tang, K. et al., "Matrix-assisted laser desorption/ionization mass spectrometry of immobilized duplex DNA probes", *Nucleic Acids Research*, vol. 23, No. 16 (1995), pp. 3126-3131.
Tanksley, S.D. et al., "RFLP mapping in plant breeding: new tools for an old science", Bio/Technology, vol. 7 (Mar. 1989), pp. 257-264.
Taranenko, N.I. et al., "Laser desorption mass spectrometry for point mutation detection", *Genetic Analysis: Biomolecular Engineering*, vol 13 (1996), pp. 87-94.
Vos, P. et al., "AFLP: a new technique for DNA fingerprinting", *Nucleic Acids Research*, vol. 23, No. 21 (1995), pp. 4407-4414.
Wallace, R.B. et al., "Hybridization of synthetic oligodeoxyribonucleotides to $\Phi_X$ 174 DNA: the effect of single base pair mismatch", *Nucleic Acids Research*, vol. 6, No. 11 (1979), pp. 3543-3557.
Weber, J.L. et al., "Abundant Class of Human DNA Polymorphisms Which Can Be Typed Using the Polymerase Chain Reaction", *Am. J. Hum. Genet.*, vol. 44 (1989), pp. 388-396.
Williams, J.G.K. et al., "DNA polymorphisms amplified by arbitrary primers are useful as genetic markers", *Nucleic Acids Research*, vol. 18, No. 22 (1990), pp. 6531-6535.
Xu, L. et al., "Electrophore Mass Tag Dideoxy DNA Sequencing", *Anal. Chem.*, vol. 69, No. 17 (1997), pp. 6595-3602.
Zhang, Y-H et al., "RNA Analysis from Newborn Screening Dried Blood Specimens", *Human Genetics*, vol. 89 (1992), pp. 311-314.
Abravaya K. et al., "Detection of point mutations with a modified ligase chain reaction (Gap-LCR)", *Nucleic Acids Res.* (1995) 23(4):675-682.
Barany F. "Genetic disease detection and DNA amplification using cloned thermostable ligase", Proc Natl Acad Sci. USA (1991) 88: 189-193.
Beckmann J.S. et al., "Survey of human and rat microsatellites", Genomics (1992) 12(4):627-631.
Beggs A.H. et al., "Detection of 98% of DMD/BMD gene deletions by polymerase chain reaction", Hum Genet. (1990) 86(1):45-48.
Chamberlain J.S. et al. "Deletion screening of the Duchenne muscular dystrophy locus via multiplex DNA amplification", Nucleic Acid Res. (1988) 16(23):11141-11156.
Chamberlain et al. 1989 ("Multiple PCR for the diagnosis of Duchenne muscular dystrophy", In PCR Protocols, A Guide to Methods and Application [Eds. Innis M.A. et al.], Chapter 33; pp. 272-281. Academic Press, San Diego, CA.
Clemens P.R., et al. "Carrier Detection and Prenatal Diagnosis in Duchenne and Becker Muscular Dystrophy Families, Using Dinucleotide Repeat Polymorphisms", Am. J. Hum. Genet. 49: 951-960.

Cheng J. et al., "Chip PCR. II. Investigation of different PCR amplification systems in microfabricated silicon-glass chips", Nucl Acids Res. (1996) 24(2):380-385.
Cohen A.S. et al., Chapter 3—"Emerging technologies for sequencing antisense oligonucleotides: capillary electrophoresis and mass spectrometry", Advances in Chromatography [Brown et al. Eds]. (1996) 36:127-164.
Cotton R.G.H. et al., "Reactivity of cytosine and thymine in single-base-air mismatches with hydroxylamine and osmium tetroxide and its application to the study of mutations", Proc Natl Acad Sci. USA (1988) 85:4397-4401.
Cotton R.G.H. et al., "Current methods of mutation detection", Mutation Res. (1993) 285(1):125-144.
Covone A.E. et al. "Screening Duchenne and Becker Muscular Dystrophy Patients for Deletions in 30 Exons of the Dystrophin Gene by Three-Multiplex PCR", Am J Hum Genet. (1992) 51:675-677.
Cronin T. et al., "Cystic Fibrosis Mutation Detection by Hybridization to Light-Generated DNA Probe Arrays", Hum Mutation (1996) 7:244-255.
Cull M. et al., "Preparation of Extracts from Prokaryotes", in Deutscher (ed.), Methods in Enzymology 1990, vol. 182, pp. 147-153.
Dignam J.D., "Preparation of Extracts from Higher Eukaryotes", in Deutscher (ed.), Methods in Enzymology 1990, vol. 182, pp. 194-203.
Edwards A. et al., "DNA typing and genetic mapping with trimeric and tetrameric tandem repeats", Am J Hum Genet (1991) 49(4):746-756.
Edwards A.L. et al., "Genetic variation at five trimeric and tetrameric tandem repeat loci in four human population groups", Genomics (1992) 12(2):241-253.
Estivill X. et al. "Prenatal diagnosis of cystic fibrosis by multiplex PCR of mutation and microsatellite alleles", Lancet (1991) 338(8764): 458.
Ferrie R.M. et al., "Development, Multiplexing and Application of ARMS Tests for Common Mutations in the CFTR Gene", Am J Hum Genet. (1992) 51:251-262.
Fodor P.A. et al., "Multiplexed biochemical assays with biological chips", Nature (1993) 421364:555-556.
Fortina P. et al. "Non-radioactive detection of the most common mutations in the cystic fibrosis transmembrane conductance regulator gene by multiplex allele-specific polymerase chain reaction", Hum Genet. (1992) 90:375-378.
Gasparini P. et al., "Restriction site generating-polymerase chain reaction (RG-PCR) for the probeless detection of hidden genetic variation: application to the study of some common cystic fibrosis mutations" Mol Cell Probes (1992) 6:1-7.
Gegenheimer P., "Preparation of Extracts from Plants", in Deutscher (ed.), Methods in Enzymology 1990, vol. 182, pp. 174-193.
Gibbs R.A. et al. "Identification of mutations leading to the Lesch-Nyhan Syndrome by automated direct DNA sequencing of in vitro amplified cDNA", PNAS USA (1989) 86:1919-1923.
Guatelli J.C. et al., "Isothermal, in vitro amplification of nucleic acids by a multienzyme reaction modeled after retroviral replication", Proc. Natl. Acad. Sci. USA (1990) 87:1874-1878.
Hacia J.G. et al., "Detection of heterozygous mutations in BRCA1 using high density oligonucleotide arrays and two-colour fluorescence analysis", Nat Genet. (1996) 14(4):441-447.
Hacia J.G. et al., "Evolutionary sequence comparisons using high-density oligonucleotide arrays", Nat Genet (Feb. 1998) 18(2):155-158.
Hammond H.A. et al., "Evaluation of 13 Short Tandem Repeat Loci for Use in Personal Identification Applications", Am J Hum Genet. (1994) 55: 175-189.
Hayashi K., "PCR-SSCP: A Method for Detection of Mutations", Genet Anal Tech Appl. (1992) 9(3):73-79.
Hsu I.C. et al., "Detection of DNA point mutations with DNA mismatch repair enzymes", Carcinogenesis (1994) 15(8):1657-1662.
Jazwinski S.M., "Preparation of Extracts from Yeast", in Deutscher (ed.), Methods in Enzymology 1990, vol. 182, pp. 154-174.

(56) References Cited

OTHER PUBLICATIONS

Keen J. et al., "Rapid detection of single base mismatches as heteroduplexes on Hydrolink gels", Trends Genet. (1991) 7(1): 5.
Kimpton C.P. et al., "Automated DNA Profiling Employing Multiplex Amplification of Short Tandem Repeat Loci", PCR Methods and Applications (1993) 3:13-22.
Kozal M.J. et al., Extensive polymorphisms observed in HIV-1 clade B protease gene using high-density oligonucleotide arrays, Nat Med. (Jul. 1996) 2(7):753-759.
Kwon D.Y. et al., "Transcription-based amplification system and detection of amplified human immunodeficiency virus type 1 with a bead-based sandwich hybridization format", Proc. Natl. Acad. Sci. USA (1989) 86:1173-1177.
Landegren U. et al., "A ligase-mediated gene detection technique", Science (1988) 241(4869):1077-1080.
Lipshutz R.J. et al., Using Oligonucleotide Probe Arrays to Access Genetic Diversity, BioTechniques (1995) 19(3):442-447.
Litt M. et al., "A hypervariable Microsatellite Revealed by In Vitro Amplification of a Dinucleotide Repeat within the Cardiac Muscle Actin Gene", Am J Hum Genet. (1989) 44(3):397-401.
Lizardi et al., "Exponential Amplification of Recombinant-RNA Hybridization Probes", Bio/Technology (Oct. 1988); 6:1197-1202.
Lohmann D. et al., "Detection of small RB1 gene deletions in retinoblastoma by multiplex PCR and high-resolution gel electrophoresis", Hum Genet. (1992) 89: 49-53.
Maxam A.M. et al., "A new method for sequencing DNA", Proc Natl Acad Sci USA (1977) 74(2):560-564.
Morral N. et al., "Short Communication: Multiplex PCR Amplification of Three Microsatellites within the CFTR Gene", Genomics (1992) 51:1362-1364.
Myers R.M. et al., "Detection of single base substitutions by ribonuclease cleavage at mismatches in RNA: DNA duplexes", Science (1985) 230(4731):1242-1246.
Myers R.M. et al., "Detection of single base substitutions in total genomic DNA", Nature (1985) 313(6002):495-498.
Nakamura Y. et al., "Variable number of tandem repeat (VNTR) markers for human gene mapping", Science (1987) 235(4796):1616-1622.
Nakazawa H. et al., "UV and skin cancer: Specific p53 gene mutation in normal skin as a biologically relevant exposure measurement", Proc Natl Acad Sci. USA (1994) 91:360-364.
Ozols J., "Preparation of Membrane Fractions" in Deutscher (ed.), Methods in Enzymology 1990, vol. 182, pp. 225-235.
Pastinen T. et al., "Minisequencing: A Specific Tool for DNA Analysis and Diagnostics on Oligonucleotide Arrays", Genome Res. (Jun. 1997) 7(6):606-614.

Pease A.C. et al., "Light-generated oligonucleotide arrays for rapid DNA sequence analysis", Proc Natl Acad Sci. USA (1994) 91(11):5022-5026.
Rosenbaum V. et al., "Temperature-gradient gel electrophoresis—Thermodynamic analysis of nucleic acids and proteins in purified form and in cellular extracts", Biophys Chem. (1987) 26:235-246.
Prossner J., "Detecting single-base mutations", Trends Biotech. (1993) 11:238-246.
Saiki R.K. et al., "Analysis of enzymatically amplified beta-globin and HLA-DQalpha DNA with allele-specific oligonucleotide probes", Nature (1986) 324(6093):163-166.
Saiki R.K. et al., "Genetic analysis of amplified DNA with immobilized sequence-specific oligonucleotide probes", Proc Natl Acad Sci. USA (1989) 86:6230-6234.
Saleeba J.A. et al., "Chemical Cleavage of Mismatch to Detect Mutations", in Mutagenesis and Gene Disruption by R. Wu [Ed.], Meth Enzymol. Recombinant DNA (1992) 217:286-295.
Sanger F. et al., "DNA sequencing with chain-terminating inhibitors", Proc Natl Acad Sci. USA (1977) 74(12):5463-5467.
Schena M. et al., "Quantitative Monitoring of Gene Expression Patterns with a Complementary DNA Microarray", Science (1995) 270: 467-470.
Schena M. et al., "Parallel human genome analysis: Microarray-based expression monitoring of 1000 genes", PNAS (1996) 93(2):10614-10619.
Schwartz L.S. et al., "Fluorescent Multiplex Linkage Analysis and Carrier Detection for Duchenne/Becker Muscular Dystrophy", Am J. Hum. Genet. (1992) 51:721-729.
Shumaker J.M. et al., "Mutation detection by solid phase primer extension", Hum Mutat. (1996) 7(4):346-354.
Southern E.M., "DNA chips: Analysing sequence by hybridization to aolilgonucleotides on a large scale", Trends Genet. (1996) 12(3):110-115.
Stimpson D.I. et al., "Real-time detection of DNA hybridization and melting on oligonucleotide arrays by using optical wave guides", Proc Natl Acad Sci. USA (1995) 92(14):6379-6383.
Storrie B. et al., "Isolation of Subcellular Organelles" in Deutscher (ed.), Methods in Enzymology 1990, vol. 182, pp. 203-225.
Tautz D., "Hypervariability of simple sequences as a general source for polymorphic DNA markers", Nucleic Acids Res. (1989) 17(16):6463-6471.
Wang J. et al., "Nucleic-acid immobilization, recognition and detection at chronopotentiometric DNA chips", Biosens Bioelectron. (1997) 12(7):587-599.
Wang D.G. et al., "Large-scale identification, mapping, and genotyping of single-mucleotide polymorphisms in the human genome", Science (May 1998); 280(5366):1077-1082.
Gibbs R.A. et al., "Detection of single DNA base differences by competitive Oligonucleotide priming", Nucl Acids Res. (1989) 17(7):2437-2448.

* cited by examiner

SEQUENCE LISTING

<160> NUMBER OF SEQ ID NOS: 53

<210> SEQ ID NO 1
<211> LENGTH: 19
<212> TYPE: DNA
<213> ORGANISM: Artificial Sequence
<220> FEATURE:
<223> OTHER INFORMATION: primer

<400> SEQUENCE: 1
actgcagtcc aatctgggt                                                   19

<210> SEQ ID NO 2
<211> LENGTH: 20

```
<212> TYPE: DNA
<213> ORGANISM: Artificial Sequence
<220> FEATURE:
<223> OTHER INFORMATION: primer

<400> SEQUENCE: 2
atgaaatcaa cagaggcttg                                              20

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
gggtgatttt cctctttggt                                              20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
tgattccaat catagccaca                                              20

<210> SEQ ID NO 5
<211> LENGTH: 25
<212> TYPE: DNA
<213> ORGANISM: Artificial Sequence
<220> FEATURE:
<223> OTHER INFORMATION: primer

<400> SEQUENCE: 5
tgtcatagtt tagaacgaac taacg                                        25

<210> SEQ ID NO 6
<211> LENGTH: 23
<212> TYPE: DNA
<213> ORGANISM: Artificial Sequence
<220> FEATURE:
<223> OTHER INFORMATION: primer

<400> SEQUENCE: 6
ctgaggtatc aaaaactcag agg                                          23

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
acagaagtct gggatgtgga                                              20

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
```
gcccaaaaag acagacagaa                                          20

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
gatcccaagc tcttcctctt                                          20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
acgtttgtgt gtgcatctgt                                          20

<210> SEQ ID NO 11
<211> LENGTH: 8
<212> TYPE: DNA
<213> ORGANISM: Artificial Sequence
<220> FEATURE:
<223> OTHER INFORMATION: exemplary motif

<400> SEQUENCE: 11 gtgtgtgt                                                        8

<210> SEQ ID NO 12
<211> LENGTH: 18
<212> TYPE: DNA
<213> ORGANISM: Artificial Sequence
<220> FEATURE:
<223> OTHER INFORMATION: exemplary motif

<400> SEQUENCE: 12
cagcagcagc agcagcag                                            18

<210> SEQ ID NO 13
<211> LENGTH: 329
<212> TYPE: DNA
<213> ORGANISM: Homo sapiens

<400> SEQUENCE: 13 aattttgta tttttttag agacggggtt tcaccatgtt ggtcaggctg actatggagt     60
tattttaagg ttaatatata taagggtat gatagaacac ttgtcatatt tagaacgaac   120
taacgataga tagatagata gatagataga tagatagata gatagataga tagacagatt   180
gatagttttt ttttatctca ctaaatagtc tatagtaaac atttaattac caatatttgg   240
tgcaattctg tcaatgagga taaatgtgga atcgttataa ttcttaagaa tatatattcc   300
ctctaatttt tatacctgat tttaaggcc                                    329

<210> SEQ ID NO 14
<211> LENGTH: 52
<212> TYPE: DNA
<213> ORGANISM: Artificial Sequence
<220> FEATURE:
<223> OTHER INFORMATION: PCR product

<400> SEQUENCE: 14
tctatctgtc tgtctatcta tctatctatc tatctatcta tctatctatc ta            52

<210> SEQ ID NO 15
<211> LENGTH: 56
<212> TYPE: DNA
<213> ORGANISM: Artificial Sequence
<220> FEATURE:
<223> OTHER INFORMATION: PCR product

<400> SEQUENCE: 15
tctatctgtc tgtctatcta tctatctatc tatctatcta tctatctatc tatcta        56

<210> SEQ ID NO 16
<211> LENGTH: 60
<212> TYPE: DNA
<213> ORGANISM: Artificial Sequence
<220> FEATURE:
<223> OTHER INFORMATION: PCR product

<400> SEQUENCE: 16
tctatctgtc tgtctgtcta tctatctatc tatctatcta tctatctatc tatctatcta    60

<210> SEQ ID NO 17
<211> LENGTH: 60
<212> TYPE: DNA
<213> ORGANISM: Artificial Sequence
<220> FEATURE:
<223> OTHER INFORMATION: PCR product

<400> SEQUENCE: 17
tctatctgtc tgtctatcta tctatctatc tatctatcta tctatctatc tatctatcta    60

<210> SEQ ID NO 18
<211> LENGTH: 64
<212> TYPE: DNA
<213> ORGANISM: Artificial Sequence
<220> FEATURE:
<223> OTHER INFORMATION: PCR product

<400> SEQUENCE: 18
tctatctgtc tgtctgtcta tctatctatc tatctatcta tctatctatc tatctatcta    60
tcta                                                                  64

<210> SEQ ID NO 19
<211> LENGTH: 64
<212> TYPE: DNA
<213> ORGANISM: Artificial Sequence
<220> FEATURE:
<223> OTHER INFORMATION: PCR product

<400> SEQUENCE: 19
tctatctgtc tgtctatcta tctatctatc tatctatcta tctatctatc tatctatcta    60
tcta                                                                  64

<210> SEQ ID NO 20
<211> LENGTH: 68
<212> TYPE: DNA
<213> ORGANISM: Artificial Sequence
<220> FEATURE:
<223> OTHER INFORMATION: PCR product

<400> SEQUENCE: 20
tctatctgtc tgtctgtcta tctatctatc tatctatcta tctatctatc tatctatcta    60
tctatcta                                                              68

<210> SEQ ID NO 21
<211> LENGTH: 68
<212> TYPE: DNA
<213> ORGANISM: Artificial Sequence
<220> FEATURE:
<223> OTHER INFORMATION: PCR product

<400> SEQUENCE: 21
tctatctgtc tgtctatcta tctatctatc tatctatcta tctatctatc tatctatcta    60
tctatcta                                                              68

<210> SEQ ID NO 22
<211> LENGTH: 72
<212> TYPE: DNA
<213> ORGANISM: Artificial Sequence
<220> FEATURE:
<223> OTHER INFORMATION: PCR product

<400> SEQUENCE: 22
tctatctgtc tgtctgtcta tctatctatc tatctatcta tctatctatc tatctatcta    60
tctatctatc ta                                                         72

<210> SEQ ID NO 23
<211> LENGTH: 76
<212> TYPE: DNA
<213> ORGANISM: Artificial Sequence
<220> FEATURE:
<223> OTHER INFORMATION: PCR product

<400> SEQUENCE: 23
tctatctgtc tgtctgtcta tctatctatc tatctatcta tctatctatc tatctatcta    60
tctatctatc tatcta                                                     76

<210> SEQ ID NO 24
<211> LENGTH: 28
<212> TYPE: DNA
<213> ORGANISM: Artificial Sequence
<220> FEATURE:
<223> OTHER INFORMATION: PCR product

<400> SEQUENCE: 24
agatagatag atagatagat agatagat                                        28

<210> SEQ ID NO 25
<211> LENGTH: 32
<212> TYPE: DNA
<213> ORGANISM: Artificial Sequence
<220> FEATURE:
<223> OTHER INFORMATION: PCR product

<400> SEQUENCE: 25
agatagatag atagatagat agatagatag at                                   32

<210> SEQ ID NO 26
<211> LENGTH: 36
<212> TYPE: DNA
<213> ORGANISM: Artificial Sequence
<220> FEATURE:
<223> OTHER INFORMATION: PCR product

<400> SEQUENCE: 26
agatagatag atagatagat agatagatag atagat                               36

```
<210> SEQ ID NO 27
<211> LENGTH: 40
<212> TYPE: DNA
<213> ORGANISM: Artificial Sequence
<220> FEATURE:
<223> OTHER INFORMATION: PCR product

<400> SEQUENCE: 27
agatagatag atagatagat agatagatag atagatagat                    40

<210> SEQ ID NO 28
<211> LENGTH: 44
<212> TYPE: DNA
<213> ORGANISM: Artificial Sequence
<220> FEATURE:
<223> OTHER INFORMATION: PCR product

<400> SEQUENCE: 28
agatagatag atagatagat agatagatag atagatagat agat               44

<210> SEQ ID NO 29
<211> LENGTH: 48
<212> TYPE: DNA
<213> ORGANISM: Artificial Sequence
<220> FEATURE:
<223> OTHER INFORMATION: PCR product

<400> SEQUENCE: 29
agatagatag atagatagat agatagatag atagatagat agatagat           48

<210> SEQ ID NO 30
<211> LENGTH: 52
<212> TYPE: DNA
<213> ORGANISM: Artificial Sequence
<220> FEATURE:
<223> OTHER INFORMATION: PCR product

<400> SEQUENCE: 30
agatagatag atagatagat agatagatag atagatagat agatagatag at      52

<210> SEQ ID NO 31
<211> LENGTH: 56
<212> TYPE: DNA
<213> ORGANISM: Artificial Sequence
<220> FEATURE:
<223> OTHER INFORMATION: PCR product

<400> SEQUENCE: 31
agatagatag atagatagat agatagatag atagatagat agatagatag atagat  56

<210> SEQ ID NO 32
<211> LENGTH: 60
<212> TYPE: DNA
<213> ORGANISM: Artificial Sequence
<220> FEATURE:
<223> OTHER INFORMATION: PCR product

<400> SEQUENCE: 32
agatagatag atagatagat agatagatag atagatagat agatagatag atagatagat  60

<210> SEQ ID NO 33
<211> LENGTH: 24
<212> TYPE: DNA
<213> ORGANISM: Artificial Sequence
<220> FEATURE:
```

<223> OTHER INFORMATION: PCR product

<400> SEQUENCE: 33
gatagataga tagatagata gata                                              24

<210> SEQ ID NO 34
<211> LENGTH: 28
<212> TYPE: DNA
<213> ORGANISM: Artificial Sequence
<220> FEATURE:
<223> OTHER INFORMATION: PCR product

<400> SEQUENCE: 34
gatagataga tagatagata gatagata                                          28

<210> SEQ ID NO 35
<211> LENGTH: 32
<212> TYPE: DNA
<213> ORGANISM: Artificial Sequence
<220> FEATURE:
<223> OTHER INFORMATION: PCR product

<400> SEQUENCE: 35
gatagataga tagatagata gatagataga ta                                     32

<210> SEQ ID NO 36
<211> LENGTH: 36
<212> TYPE: DNA
<213> ORGANISM: Artificial Sequence
<220> FEATURE:
<223> OTHER INFORMATION: PCR product

<400> SEQUENCE: 36
gatagataga tagatagata gatagataga tagata                                 36

<210> SEQ ID NO 37
<211> LENGTH: 40
<212> TYPE: DNA
<213> ORGANISM: Artificial Sequence
<220> FEATURE:
<223> OTHER INFORMATION: PCR product

<400> SEQUENCE: 37
gatagataga tagatagata gatagataga tagatagata                             40

<210> SEQ ID NO 38
<211> LENGTH: 44
<212> TYPE: DNA
<213> ORGANISM: Artificial Sequence
<220> FEATURE:
<223> OTHER INFORMATION: PCR product

<400> SEQUENCE: 38
gatagataga tagatagata gatagataga tagatagata gata                        44

<210> SEQ ID NO 39
<211> LENGTH: 48
<212> TYPE: DNA
<213> ORGANISM: Artificial Sequence
<220> FEATURE:
<223> OTHER INFORMATION: PCR product

<400> SEQUENCE: 39
gatagataga tagatagata gatagataga tagatagata gatagata                    48

```
<210> SEQ ID NO 40
<211> LENGTH: 52
<212> TYPE: DNA
<213> ORGANISM: Artificial Sequence
<220> FEATURE:
<223> OTHER INFORMATION: PCR product

<400> SEQUENCE: 40
gatagataga tagatagata gatagataga tagatagata gatagataga ta         52

<210> SEQ ID NO 41
<211> LENGTH: 56
<212> TYPE: DNA
<213> ORGANISM: Artificial Sequence
<220> FEATURE:
<223> OTHER INFORMATION: PCR product

<400> SEQUENCE: 41
gatagataga tagatagata gatagataga tagatagata gatagataga tagata     56

<210> SEQ ID NO 42
<211> LENGTH: 28
<212> TYPE: DNA
<213> ORGANISM: Artificial Sequence
<220> FEATURE:
<223> OTHER INFORMATION: PCR product

<400> SEQUENCE: 42
tatctatcta tctatctatc tatctatc                                    28

<210> SEQ ID NO 43
<211> LENGTH: 32
<212> TYPE: DNA
<213> ORGANISM: Artificial Sequence
<220> FEATURE:
<223> OTHER INFORMATION: PCR product

<400> SEQUENCE: 43
tatctatcta tctatctatc tatctatcta tc                               32

<210> SEQ ID NO 44
<211> LENGTH: 36
<212> TYPE: DNA
<213> ORGANISM: Artificial Sequence
<220> FEATURE:
<223> OTHER INFORMATION: PCR product

<400> SEQUENCE: 44
tatctatcta tctatctatc tatctatcta tctatc                           36

<210> SEQ ID NO 45
<211> LENGTH: 40
<212> TYPE: DNA
<213> ORGANISM: Artificial Sequence
<220> FEATURE:
<223> OTHER INFORMATION: PCR product

<400> SEQUENCE: 45
tatctatcta tctatctatc tatctatcta tctatctatc                       40

<210> SEQ ID NO 46
<211> LENGTH: 44
<212> TYPE: DNA
<213> ORGANISM: Artificial Sequence
<220> FEATURE:
<223> OTHER INFORMATION: PCR product
```

```
<400> SEQUENCE: 46
tatctatcta tctatctatc tatctatcta tctatctatc aatc                44

<210> SEQ ID NO 47
<211> LENGTH: 44
<212> TYPE: DNA
<213> ORGANISM: Artificial Sequence
<220> FEATURE:
<223> OTHER INFORMATION: PCR product

<400> SEQUENCE: 47
tatctatcta tctatctatc tatctatcta tctatctatc tatc                44

<210> SEQ ID NO 48
<211> LENGTH: 48
<212> TYPE: DNA
<213> ORGANISM: Artificial Sequence
<220> FEATURE:
<223> OTHER INFORMATION: PCR product

<400> SEQUENCE: 48
tatctatcta tctatctatc tatctatcta tctatctatc tatctatc            48

<210> SEQ ID NO 49
<211> LENGTH: 52
<212> TYPE: DNA
<213> ORGANISM: Artificial Sequence
<220> FEATURE:
<223> OTHER INFORMATION: PCR product

<400> SEQUENCE: 49
tatctatcta tctatctatc tatctatcta tctatctatc tatctatcta tc       52

<210> SEQ ID NO 50
<211> LENGTH: 56
<212> TYPE: DNA
<213> ORGANISM: Artificial Sequence
<220> FEATURE:
<223> OTHER INFORMATION: PCR product

<400> SEQUENCE: 50
tatctatcta tctatctatc tatctatcta tctatctatc tatctatcta tctatc   56

<210> SEQ ID NO 51
<211> LENGTH: 60
<212> TYPE: DNA
<213> ORGANISM: Artificial Sequence
<220> FEATURE:
<223> OTHER INFORMATION: PCR product

<400> SEQUENCE: 51
tatctatcta tctatctatc tatctatcta tctatctatc tatctatcta tctatctatc  60

<210> SEQ ID NO 52
<211> LENGTH: 20
<212> TYPE: DNA
<213> ORGANISM: Artificial Sequence
<220> FEATURE:
<223> OTHER INFORMATION: PCR product

<400> SEQUENCE: 52
gatagataga tagatagata                                           20

<210> SEQ ID NO 53
<211> LENGTH: 60
```

```
<212> TYPE: DNA
<213> ORGANISM: Artificial Sequence
<220> FEATURE:
<223> OTHER INFORMATION: PCR product

<400> SEQUENCE: 53
gatagataga tagatagata gatagataga tagatagata gatagataga tagatagata    60
```

METHODS FOR SAMPLE TRACKING

CLAIM OF PRIORITY

This application is a continuation of U.S. patent application Ser. No. 10/360,854, filed Feb. 10, 2003, now abandoned. The disclosure of the parent application is incorporated herein by reference in its entirety.

1. INTRODUCTION

The present invention relates generally to the emerging field of human, animal or plant DNA fingerprinting. The methods and apparatus of the invention have application in the fields of diagnostic medicine, disease diagnosis in animals and plants, identification of genetically inherited diseases in humans, family relationship analysis, forensic analysis, and microbial typing. In a preferred embodiment, the invention relates to methods and apparatus for the simultaneous analysis and tracking of biological samples.

2. BACKGROUND OF THE INVENTION

It is known that there are simple nucleotide sequences in the human genome that can occur in different numbers of repeats in different individuals, giving rise to a range of different alleles or variants of different length that can be used as genetic markers to typify the DNA of an individual. It is these genetic markers that DNA diagnostic laboratories use in molecular diagnostics procedures for the identification and characterization of diseased genes. Such genetic markers are also use for precision of DNA typing of individuals in the field of forensic science.

In general, tandem repeat minisatellite and microsatellite regions in vertebrate DNA frequently show high levels of allelic variability in the number of repeat units. These highly informative genetic markers have found widespread applications in population genetics, forensic science, medicine and other natural scientific studies. For example, these markers can be used for linkage analysis, determination of kinship in paternity and immigration disputes and for individual identification in forensic medicine. In a minisatellite system, a core DNA sequence unit is usually 15 or more base pairs. To date most studies and applications of such systems have relied on Southern blot estimation of allele length, which requires at least 50 ng of relatively undegraded DNA. It is often very difficult to extract such large amounts of DNA from many forensic samples such as blood and semen stains.

In recent years, the discovery and development of polymorphic short tandem repeats (STRs) and Variable Number Tandem Repeats (VNTRs) as genetic markers have stimulated progress in the development of linkage maps, the identification and characterization of diseased genes, and the simplification and precision of DNA typing of individuals.

Many loci in the human genome contain a polymorphic STR region. STR loci consist of short, repetitive sequence elements on the order of 3 to 7 base pairs in length. It is estimated that there are roughly 2,000,000 expected trimeric and tetrameric STRs present as frequently as once every 15 kilobases (kb) in the human genome (Edwards et al. 1991 (Am J Hum Genet 49:746-756); Beckmann and Weber 1992 (Genomics 12:627-631)). Nearly half of the STR loci studied by Edwards et al. (1991) are polymorphic, which provides a rich source of genetic markers. Variation in the number of repeat units at a particular locus is responsible for the observed polymorphism reminiscent of VNTR loci (Nakamura et al. 1987 (Science 235:1616-1622) and minisatellite loci (Jeffreys et al. 1985 (Nature 316:76-79)), which contain longer repeat units, and microsatellite or dinucleotide repeat loci (Litt and Luty 1989 (Am J Hum Genet 44:397-401), Tautz 1989 (Nucleic Acids Res. 17:6463-6471), Weber and May 1989 (Am J Hum Genet 44:388-396), Beckmann and Weber 1992 (Genomics 12:627-631)).

Such polymorphic STR loci are extremely useful markers for human identification, paternity testing and genetic mapping. STR loci may be amplified via the polymerase chain reaction (PCR) by employing specific primer sequences identified in the regions flanking the tandem repeat. Alleles of these loci can be differentiated by the number of copies of the repeat sequence contained within the amplified region and are distinguished from one another following electrophoretic separation by any suitable detection method including, for example, radioactivity, fluorescence, silver stain, and color. To minimize labor, materials and analysis time, it is desirable to analyze multiple loci and/or more samples simultaneously. One approach involves amplification of multiple loci simultaneously in a single reaction. Such "multiplex" amplifications have been described extensively in the literature, for example, in the analysis or genes related to human genetic diseases such as Duchenne Muscular Dystrophy (Chamberlain et al. 1988 (Nucleic Acid Res 16: 11141-11156), Chamberlain et al. 1989 ("Multiple PCR for the diagnosis of Duchenne muscular dystrophy," In PCR Protocols, A Guide to Methods and Application (ed. Gelfand, D. H., et al.) pp. 272-281. Academic Press, San Diego, Calif.), Beggs et al. 1990 (Hum. Genet. 86: 45-48), Clemens et al. 1991 (Am J. Hum. Genet. 49: 951-960), Schwartz et al. 1992 (Am J. Hum. Genet. 51: 721-729), Covone et al. 1992 (Am. J. Hum. Genet. 51: 675-677)), Lesch-Nyhan Syndrome (Gibbs et al. 1990), Cystic Fibrosis (Estivill et al. 1991 (Lancet 338: 458), Fortina et al. 1992 (Hum Genet. 90: 375-378), Ferrie et al. 1992 (Am. J. Hum. Genet. 51: 251-262), Morral and Estivill, 1992 (Genomics 51:1362-1364), and Retinoblasma (Lohmann et al. 1992 (Hum. Genet. 89: 49-53)). Multiplex amplification of polymorphic microsatellite markers and STR markers have been described previously in the literature (Clemens et al. 1991 (Am J. Hum. Genet. 49: 951-960), Schwartz et al. 1992, Huang et al. 1992 (Genomics 13: 375-380), Edwards et al. 1992 (Genomics 12:241-253), Kimpton et al. 1993 (PCR Methods and Applications 3: 13-22), Hammond et al. 1994 (Am. J. Hum. Genet. 55: 175-189)).

Recently, RFLPs that have Variable Number Tandem Repeats (VNTRs) have become a method of choice for human mapping because such VNTRs tend to have multiple alleles and are genetically informative because polymorphisms are more likely to be segregating within a family. The production of fingerprints by Southern blotting with VNTRs (Jeffreys et al., Nature 316:76-79 (1985)) has proven useful in the field of forensics. There are two classes of VNTRs; one having repeat units of 9 to 40 base pairs, and the other consisting of minisatellite DNA with repeats of two or three base pairs. The longer VNTRs have tended to be in the proterminal regions of autosomes. VNTR consensus sequences may be also used to display a DNA fingerprint.

Thus, while molecular diagnostics procedures, which rely on the use of such markers as, inter alia, STRs and VNTRs, are particularly well-suited to the application of prenatal diagnosis, presymptomatic diagnosis, carrier detection, and genetic screening, there still remain major bottlenecks in molecular diagnostic laboratories including front-end tasks such as sample purification and reaction setup. To date, the major sources for concern in clinical molecular laboratories are the safety, costs and efficiency of the normal procedures for preparation of specimens, such as blood, prior to analysis. Blood specimens for clinical analyses are commonly collected in evacuated blood collection tubes. Serum or plasma may be isolated from the cellular material by centrifugation and transferred to one or more specialized sample vessels. These sample vessels are used to introduce a portion of the specimen to chemical analyzers. However, the large numbers of samples involved often presents significant problems with sample tracking and data exchange between different laboratory instruments and information management systems. A certified DNA Diagnostics Laboratory provides a chain of custody report for each sample that is to be tested. The report traces the history of each sample from the time it was collected by one of their representatives until the results are released. The DNA Diagnostics Laboratory usually relies on a computerized sample tracking system that assigns a number for each sample to ensure confidentiality and chain of custody.

To provide for proper biological sample identification, a computer readable bar code label is usually affixed to the tube containing the biological sample. The bar code label allows for electronic processing of the sample and also helps to eliminate misidentification or confusion of samples. While the use of computer-based barcodes can provide a high level of sample tracking, such barcode labels still suffer from some significant drawbacks. For example, they are susceptible to manipulation, they typically involve an additional step, they can be lost, and barcodes are not unique to the individual, etc. In addition, the time and technical constraints associated with most sample preparation protocols have heretofore impeded the rapid, cost-effective, reproducible, systematic and unequivocal identification of biological samples.

For these aforementioned reasons, what is needed in the field of diagnostic medicine and disease diagnosis is a system and method suitable for biological sample tracking without the prior possibilities of accidental misidentification of the source of the sample and any diagnostic data derived from such a sample. This application addresses these and other needs by providing a method for analyzing a biological sample to detect the presence of an infectious agent, a disease condition and/or disease predisposition while simultaneously determining the molecular barcode of the sample so as to uniquely identify the biological sample without the chance of any mishandling or misidentification. The invention also includes a microfluidic processor apparatus for use in such a method.

Citation or discussion of a reference herein shall not be construed as an admission that such is prior art to the present invention.

3. SUMMARY OF THE INVENTION

The present invention relates to methods and an apparatus for providing identification of biological samples used in diagnostic laboratories. In particular, the invention relates to methods and an apparatus for analyzing a biological sample to detect the presence of an infectious agent or disease condition and/or disease predisposition and determining the unique molecular barcode of the sample so as to uniquely identify the biological sample, thereby greatly reducing the chance of errors associated with misidentification of the biological sample or a patient record associated with the molecular barcode. In a preferred embodiment, the unique molecular barcode of the sample is determined simultaneously with the detection of the presence of an infectious agent or disease condition and/or disease predisposition. It is the particular unique combination of genetic markers associated with each individual that provides the biological sample with its unique identification and is termed its molecular barcode. The combination of amplified markers (and hence the molecular barcode) is preferably unique to the extent that the chance of another mammal exhibiting an indistinguishable combination of amplified markers is less than 1 in 10,000, for example, less than 1 in 100,000, for example, less than 1 in 1,000,000. The chance that a given population of mammals will include at least two individuals having an indistinguishable combination of amplified markers may be determined using the Hardy-Weinberg principle.

One aspect of the invention relates to a method for identifying a biological sample comprising biological material of a mammal. The method may comprise the steps of: obtaining amplification data indicative of amplification of at least two DNA markers of genomic DNA of the mammal, generating indicia indicative of the amplification data, and associating the indicia with the biological sample, whereby the indicia may be used to identify the biological sample.

The amplification data may be indicative of amplification of at least three, for example, at least five DNA markers of genomic DNA of the mammal. The DNA markers may be selected from the group consisting of the following primer pairs:

```
D3S1358
5' Primer
ACTGCAGTCCAATCTGGGT         (SEQ ID NO: 1)

3' primer
ATGAAATCAACAGAGGCTTG;       (SEQ ID NO: 2)

D5S818
5' Primer
GGGTGATTTTCCTCTTTGGT        (SEQ ID NO: 3)

3' primer
TGATTCCAATCATAGCCACA;       (SEQ ID NO: 4)

D7S820
5' Primer
TGTCATAGTTTAGAACGAACTAACG   (SEQ ID NO: 5)

3' primer
CTGAGGTATCAAAAACTCAGAGG;    (SEQ ID NO: 6)

D13S317
5' Primer
ACAGAAGTCTGGGATGTGGA        (SEQ ID NO: 7)

3' primer
GCCCAAAAAGACAGACAGAA;       (SEQ ID NO: 8)

D16S539
5' Primer
GATCCCAAGCTCTTCCTCTT        (SEQ ID NO: 9)

3' primer
ACGTTTGTGTGTGCATCTGT;       (SEQ ID NO: 10)
and
``` complementary sequences thereto.

The method may comprise the further steps of diagnosing the DNA sample to obtain a result indicative of whether the mammal is afflicted with a particular disease or disorder, or is at risk of developing a particular disease or disorder and associating the result obtained from said diagnosis step with at least one of the amplification data or indicia. Associating the result obtained from said diagnosis step with the amplification data comprises saving the amplification data to a computer readable medium, such as a computer memory or storage medium. The step of diagnosing may be performed essentially simultaneously with the step of amplification. For example, the sample may be divided into at least two portions. One of the portions is subjected to the obtaining amplification data step; the other portion is subjected to the diagnosing step. In a preferred embodiment, the steps of obtaining amplification data and diagnosing are performed using a microfluidic device. Preferably, a single microfluidic device, for example the same microfluidic chip, is used to perform the steps of dividing the sample, obtaining amplification data, and diagnosing.

The method may further comprise obtaining data indicative of the presence of a pathogen in the biological sample and associating the data indicative of the presence of the pathogen with at least one of the amplification data or indicia, whereby the indicia are indicative of the presence of the pathogen. The data indicative of the presence of the pathogen may be indicative of the type of pathogen, such as for example, whether the pathogen is a bacteria or virus. The data may also indicate further information about the pathogen, such as the type of bacteria and/or strain of bacteria.

The step of obtaining data indicative of the presence of the pathogen may be performed essentially simultaneously with the step of amplification. For example, the sample may be divided into at least two portions. One of the portions is subjected to the obtaining amplification data step; the other portion is subjected to the obtaining data indicative of the pathogen step. In a preferred embodiment, the steps of obtaining amplification data and obtaining data indicative of the pathogen are performed using a microfluidic device. Preferably, a single microfluidic device, for example the same microfluidic chip, is used to perform the steps of dividing the sample, obtaining amplification data, and obtaining data indicative of the pathogen.

Generating the indicia further may comprise printing a label comprising the indicia. The label may be secured to a container comprising at least a portion of the sample. The label may be secured to a record comprising other data related to the mammal, such as other treatments the mammal may have been or will be subjected to. Preferably, the indicia may be read using an automated reader, such as an optical bar code reader.

Another aspect of the invention relates to a method for creating a database. The database is preferably configured to allow storage and retrieval of a plurality of data records. The database may comprise a plurality of locations. For each of a plurality of mammals the method may comprise: obtaining amplification data indicative of amplification of at least two DNA markers of genomic DNA of the mammal, entering the amplification data in a first location of the database, and entering first indicia in a second location of the database, the first indicia indicative of an identity of the mammal, wherein the first and second locations are related, whereby the database may be searched using one of the amplification data or first indicia to determine the other of the amplification data or first indicia.

The method may further comprise generating second indicia indicative of at least the amplification data and associating the second indicia with a biological sample obtained from the mammal, wherein the second indicia and the database may be used to determine the identity of the mammal from which the biological sample was obtained.

In one embodiment, the method comprises, preferably for each mammal, diagnosing a DNA sample obtained from the mammal to obtain a result indicative of whether the mammal is afflicted with a particular disease or disorder, or is at risk of developing a particular disease or disorder and entering the result in a third location of the database, wherein the database may be searched using one of the amplification data or first indicia to determine the result.

Another aspect of the invention relates to a sample tracking system, comprising a device configured to at least: obtain amplification data indicative of amplification of at least two DNA markers of genomic DNA of a mammal, a processor configured to at least: generate indicia indicative of the amplification data and associate the indicia with the biological sample, whereby the indicia may be used to identify the biological sample. The device may be configured to obtain amplification data indicative of amplification of at least three DNA markers of genomic DNA of the mammal. The device may be configured to obtain amplification data indicative of amplification of at least five DNA markers of genomic DNA of the mammal.

The device may be configured to obtain data indicative of the presence of a pathogen. For example, the device may be a microfluidic device comprising at least one substrate defining a microfluidic network.

The system may be configured to provide a label comprising the indicia.

The methods and apparatus of the invention are particularly applicable to biological samples being subjected to complex multistep assays, where there exists numerous sample transfers, and where the risk for improper handling and/or labeling is considerably increased.

In accordance with the present invention there is provided a method for identification of a biological sample of a mammal, which comprises the steps of:

a) obtaining a genomic DNA sample from said mammal;

b) performing amplification of the genomic DNA sample using at least two primers for amplification of at least two DNA markers; and c) identifying the amplified DNA markers from step b), wherein the genomic DNA sample's unique combination of amplified markers represents the molecular barcode for identification of the biological sample.

In accordance with a preferred aspect of the present invention there is provided a method for identification of a biological sample of a mammal, which comprises the steps of:

a) obtaining a genomic DNA sample from said mammal;

b) performing DNA amplification of the genomic DNA sample using at least two primers for amplification of at least two DNA markers, wherein said primers are selected from the group consisting of SEQ ID NOS:1 to 10 and complementary sequences thereto; and c) identifying the amplified DNA markers from step b), wherein the genomic DNA sample's unique combination of amplified markers represents the molecular barcode for identification of the biological sample.

In yet another aspect of the present invention, a method is provided for identification of a biological sample of a subject undergoing diagnosis to determine whether the subject is afflicted with a particular disease or disorder, or is at risk of developing a particular disorder comprising a) obtaining a genomic DNA sample from a subject;

b) performing DNA amplification of the genomic DNA sample using at least two primers for amplification of at least two DNA markers;

c) identifying the amplified DNA markers of step b), wherein the genomic DNA sample's unique combination of amplified markers represents the molecular barcode for identification of the biological sample; and d) performing diagnosis of the subject's genomic DNA sample to determine whether the subject is afflicted with a particular disease or disorder, or is at risk of developing a particular disease or disorder, wherein the result obtained from said diagnosis step is thereby intimately associated with the molecular barcode of the sample of the subject being diagnosed.

In yet another aspect of the present invention, a method is provided for identification of a biological sample of a subject undergoing screening for genetic lesions or mutations to determine if the subject with a lesioned gene is at risk for a disease or disorder characterized by aberrant expression or activity of a given polypeptide comprising
 a) obtaining a genomic DNA sample from a subject;
 b) performing DNA amplification of the genomic DNA sample using at least two primers for amplification of at least two DNA markers;
 c) identifying the amplified DNA markers of step b), wherein the genomic DNA sample's unique combination of amplified markers represents the molecular barcode for identification of the biological sample;
 d) performing screening of the subject's genomic DNA sample for detection of genetic lesions or mutations in said genomic DNA sample to determine if a subject with a lesioned gene is at risk for a disease or disorder characterized by aberrant expression or activity of a given polypeptide; wherein the result obtained from said screening step is thereby intimately associated with the molecular barcode of the sample of the subject being screened.

In yet another aspect of the present invention, a method is provided for identification of a biological sample of a subject being diagnosed for the presence of a target microorganism comprising
 a) obtaining a genomic DNA sample from a subject;
 b) performing DNA amplification of the genomic DNA sample using at least two primers for amplification of at least two DNA markers; and
 c) identifying the amplified DNA markers of step b), wherein the genomic DNA sample's unique combination of amplified markers represents the molecular barcode for identification of the biological sample; and
 d) performing diagnosis of said subject to detect the presence of a target microorganism; wherein the result obtained from said diagnosis step is thereby intimately associated with the molecular barcode of the sample of the subject being diagnosed.

In yet another aspect of the present invention, a method is provided for identification of a biological sample of a subject undergoing paternity screening, genetic screening, prenatal diagnosis, presymptomatic diagnosis, disease carrier detection, or forensic chemical analysis comprising
 a) obtaining a genomic DNA sample from a subject;
 b) performing DNA amplification of the genomic DNA sample using at least two primers for amplification of at least two DNA markers;
 c) identifying the amplified DNA markers of step b), wherein the genomic DNA sample's unique combination of amplified markers represents the molecular barcode for identification of the biological sample; and
 d) performing paternity screening, genetic screening, prenatal diagnosis, presymptomatic diagnosis, disease carrier detection, forensic chemical analysis, or any combination thereof, of the subject's genomic DNA sample, wherein the result obtained from said paternity screening, genetic screening, prenatal diagnosis, presymptomatic diagnosis, disease carrier detection, or forensic chemical analysis step is thereby intimately associated with the molecular barcode of the sample of the subject being screened or diagnosed.

In a preferred embodiment of the invention, the at least two primers for the amplification of at least two markers are selected from the group consisting of

```
D3S1358
5' Primer
ACTGCAGTCCAATCTGGGT         (SEQ ID NO: 1)

3' primer
ATGAAATCAACAGAGGCTTG;       (SEQ ID NO: 2)

D5S818
5' Primer
GGGTGATTTTCCTCTTTGGT        (SEQ ID NO: 3)

3' primer
TGATTCCAATCATAGCCACA;       (SEQ ID NO: 4)

D7S820
5' Primer
TGTCATAGTTTAGAACGAACTAACG   (SEQ ID NO: 5)

3' primer
CTGAGGTATCAAAAACTCAGAGG;    (SEQ ID NO: 6)

D13S317
5' Primer
ACAGAAGTCTGGGATGTGGA        (SEQ ID NO: 7)

3' primer
GGCCAAAAAGACAGACAGAA;       (SEQ ID NO: 8)
and

D16S539
5' Primer
GATCCCAAGCTCTTCCTCTT        (SEQ ID NO: 9)

3' primer
ACGTTTGTGTGTGCATCTGT.       (SEQ ID NO: 10)
```

In yet another aspect of the present invention, methods are provided for identification of a biological sample of a subject wherein the DNA amplification of the genomic DNA sample using at least two primers results in simultaneous amplification of at least two DNA markers.

In preferred embodiments of the invention, the DNA amplification of the genomic DNA sample employs VNTR analysis, STR analysis, CTR analysis, Restriction Fragment Length Polymorphism (RFLP) analysis, allele specific oligonucleotide (ASO) analysis, denaturation temperature analysis, single strand conformation polymorphism (SSCP) analysis, amplified fragment-length polymorphism (AFLP) analysis, microsatellite or single-sequence repeat (SSR) analysis, rapid-amplified polymorphic DNA (RAPD) analysis, sequence tagged site (STS) analysis or a combination thereof.

In another aspect of the present invention, an apparatus is provided for use in the methods of the present invention.

In another aspect of the present invention a kit is provided which contains the apparatus of the present invention, at least two primers for the amplification of at least one marker, and instructions for use.

In any embodiment of the present invention, the biological sample may be selected from the group consisting of a tissue homogenate, hair, blood, semen, vaginal swabs, plasma, serum, ascites, pleural effusion, thoracentesis sample, spinal fluid, lymph fluid, bone marrow, the external sections of the skin, respiratory, intestinal, and genitourinary tracts, stool, urine, sputum, tears, saliva, fetal cells, placental cells, amniotic cells, mixtures of body fluids, vitreous humor, amniotic fluid, chorionic villus samples, blood cells, tumors, organs, tissue, and samples of in vitro cell culture constituents, a transudate, an exudate, or fluid obtained from a joint.

In any embodiment of the present invention, the DNA fingerprint may be performed by VNTR analysis, by STR analysis, by CTR analysis, by Restriction Fragment Length Polymorphism (RFLP) analysis, by allele specific oligonucleotide (ASO) analysis, by denaturation temperature analysis, by mass spectrometry analysis, by single strand conformation polymorphism (SSCP) analysis, by amplified fragment-length polymorphism (AFLP) analysis, by microsatellite or single-sequence repeat (SSR) analysis, by rapid-amplified polymorphic DNA (RAPD) analysis, by sequence tagged site (STS) analysis, by allele-specific polymerase chain reaction (ASPCR) analysis, by dynamic allele specific hybridization (DASH) analysis, or combination thereof.

The subject from which the sample is obtained may be a mammal, for example, a human, or a farm animal of agricultural importance.

For embodiments of the invention relating to plants, the biological sample may be selected from the group consisting of genomic DNA isolated from a plant, genomic DNA isolated from a plant extract, genomic DNA isolated from an isolated plant tissue, genomic DNA isolated from an isolated plant tissue extract, genomic DNA isolated from a plant cell culture, genomic DNA isolated from a plant cell culture extract, genomic DNA isolated from a recombinant cell comprising a nucleic acid derived from a plant, genomic DNA isolated from a plant seed, genomic DNA isolated from an extract of a recombinant plant cell comprising a nucleic acid derived from a plant, and DNA isolated from a chloroplast.

The pre-packaged diagnostic kits of the invention may comprise at least one nucleic acid probe or primer in one vial and reagents for diagnosis, screening or testing in another vial. The diagnostic kit may comprise at least one nucleic acid probe or primer in one vial and reagents for diagnosis, screening or testing in another vial, and a microfluidic chip for performing all or a portion of the analysis.

4. BRIEF DESCRIPTION OF THE FIGURES

Figure 4:
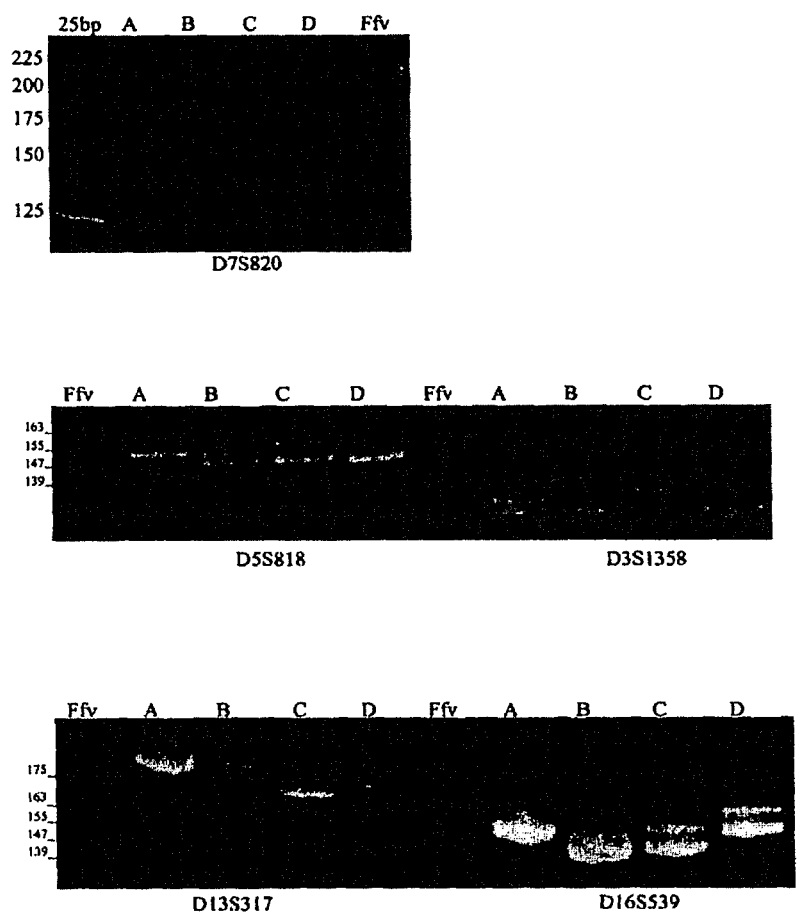

FIG. 4 depicts a photograph of an FYBR green stained polyacrylamide get of the respective STR markers. A, B, C and D are the four buccal samples. A 25 bp ladder and Ffv, the allelic ladder were used as the reference standards to determine the sizes of the alleles.

Figure 5:
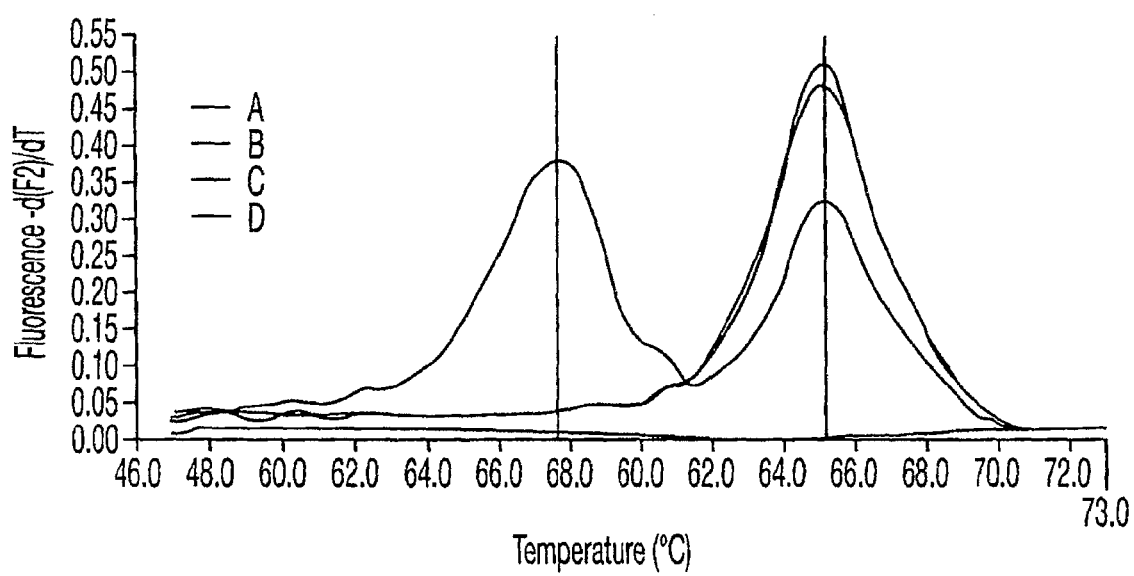

FIG. 5 depicts the genomic DNA of two samples were used to detect mutations with the Factor V Leiden mutation kit. The letter A designation represents the positive control, which is a heterozygous mutant. The letter designations B and C represent the buccal samples, which are wildtype without the mutation. The letter D designation represents the negative control without the template.

Figure 6:
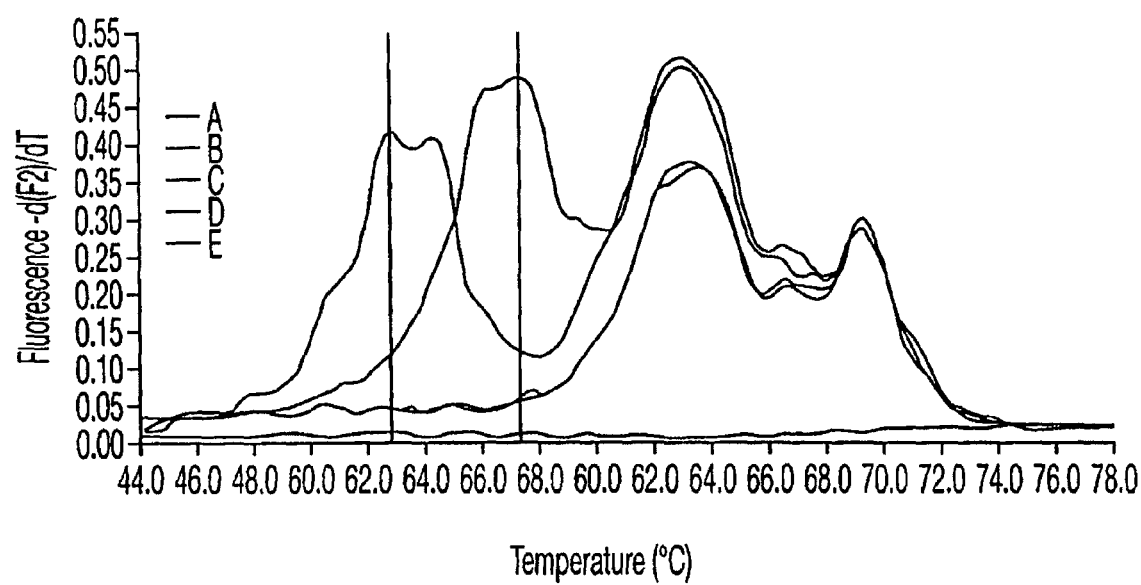

FIG. 6 depicts the same genomic DNA used in fingerprinting and in detecting the mutations in Factor V Leiden kit, was used to detect the Apo B mutations also. The letter A designation represents the heterozygous positive control with 9775 point mutation. The letter B designation represents the heterozygous positive control with 9774 mutation. The letter designations C and D represent the buccal samples used that are wildtype without any mutations; The letter E designation represents the negative control without any template.

Figure 7:
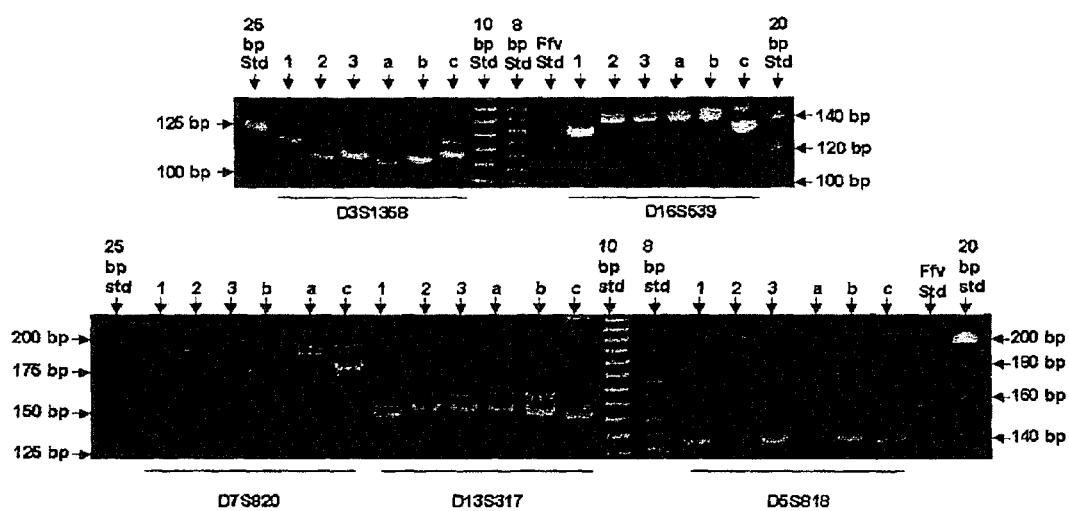

FIG. 7 depicts the FYBR green stained gels of the respective STR markers in the blind sample identification experiment conducted with the Factor V genomic DNA. Sample 1 is the heterozygous major (heterozygous mutant) individual for the Factor V mutation; sample 2 is the homozygous major (wildtype genotype) individual for the Factor V mutation; and sample 3 is the homozygous minor (homozygous mutant) individual for the Factor V mutation. 25 bp ladder and Ffv, the allelic ladder were used as the reference standards to determine the sizes of the alleles.

Figure 8:
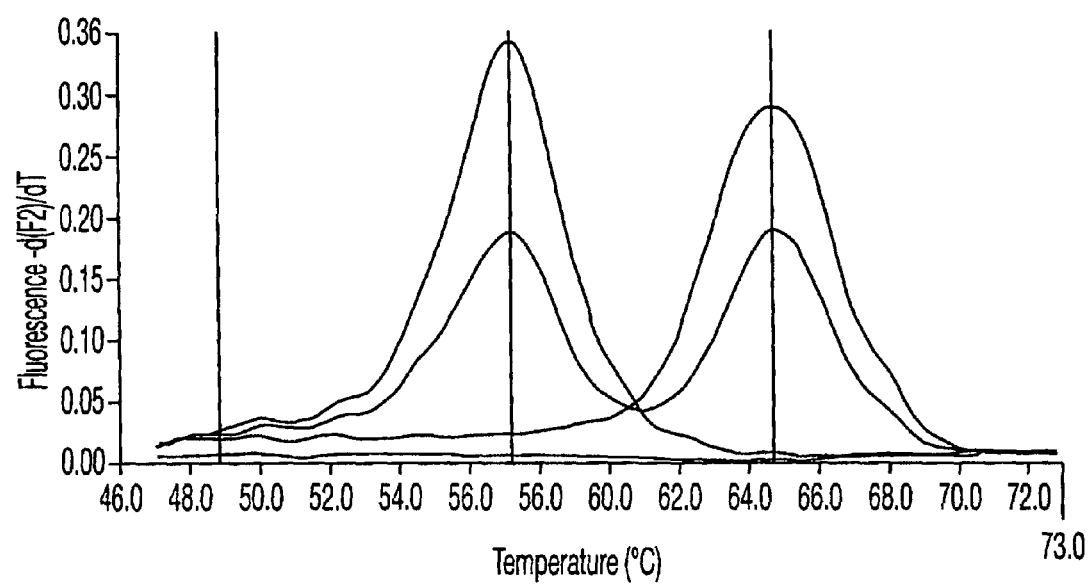

FIG. 8 depicts the analysis of the genomic DNA from the three samples (heterozygous major, homozygous major, and homozygous minor, respectively) that were used to detect mutations the Factor V genomic DNA with the Factor V Leiden mutation kit in the blind sample identification experiment.

Figure 9:
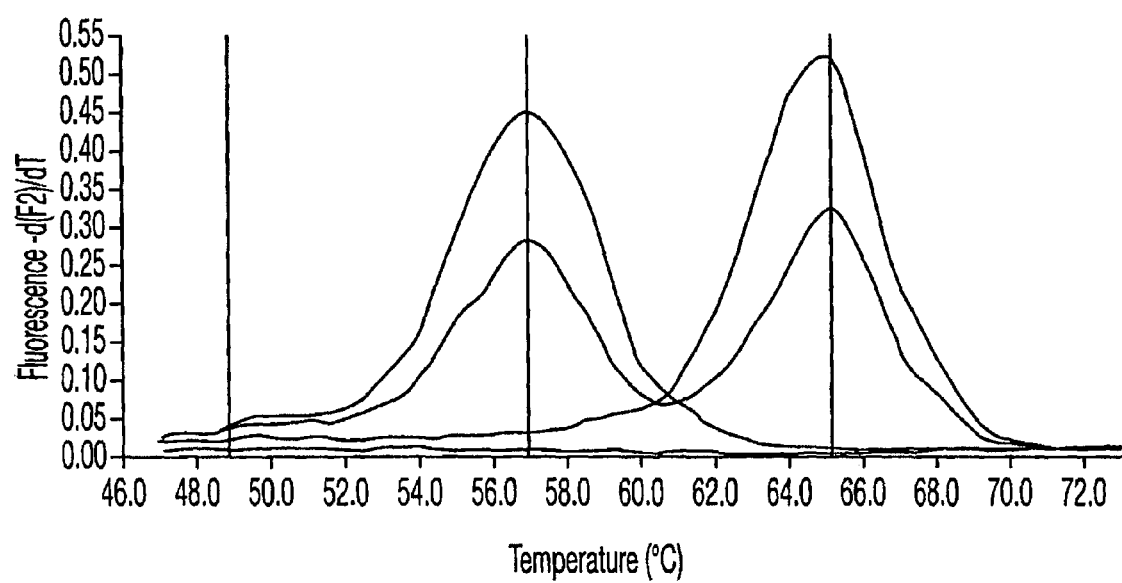

FIG. 9 depicts the analysis of the blind sample identification experiment in which samples 1-3 were masked to hide their identities and labeled arbitrarily as samples a-c.

5. DETAILED DESCRIPTION OF THE INVENTION

A major aspect of the present invention is to provide for a biological sample tracking system for use in paternity screening, genetic screening, prenatal diagnosis, presymptomatic diagnosis, carrier detection, and forensic chemical analysis laboratories. In paternity, genetic screening, prenatal diagnosis, presymptomatic diagnosis, carrier detection and forensic analysis, it is necessary that the sample and result obtained be uniquely identifiable, often even years after the analysis has been completed.

A prevalent concern of diagnostic laboratories is the considerable amount of paperwork required to track a sample through various stages of collection, preparation and analysis. In a typical study, there is about a 60% to 70% chance of clerical error on behalf of laboratory personnel, and a significant proportion of these errors result in misidentification of a sample. The collection and subsequent testing of biological samples can involve many sequential steps. Inevitably, biological samples will be stored among many similar biological samples. It is therefore important that the biological samples be uniquely identified so that information such as the time, date and place of collection and subsequent testing be determinable at all times. The identification data may be handwritten on a label, either before or after application to the sample vial containing the biological sample.

Opportunity for error exists in application of the identification labels prepared for the biological sample or, at a later stage, during the reading of handwritten labels. While printers and computer-based barcodes can theoretically be used to overcome legibility problems, there is always the chance of a typographical input error or even tampering with the printed label or barcode itself.

The heretofore unappreciated solution to this problem is to perform a DNA fingerprint or genotyping analysis at the same time as the diagnostic or prognostic analysis thereby uniquely linking the results of the diagnosis to the particular individual being diagnosed. This simultaneous genotyping step for sample identification purposes should tremendously simplify sample tracking in diagnostic laboratories.

One of the advantages of the method of the present invention is that the molecular barcode of the genomic DNA of the sample can be determined at any time during the collection or processing of a biological sample. In one embodiment, the unique molecular barcode is determined at the time of sample collection, prior to any further diagnostic, prognostic and/or target organism detection. In this way, the opportunities for misidentification and/or handling errors are considerably decreased. Once the molecular barcode of the sample is determined, a record is kept of the molecular barcode that corresponds to each sample for later sample identity verification.

In another embodiment, the unique molecular barcode of the genomic DNA sample is determined simultaneously during processing of the genomic DNA sample for diagnostic, prognostic and/or target organism detection. In this instance, because the unique molecular barcode is determined during processing of the genomic DNA sample for diagnostic, prognostic and/or target organism detection, the only requirement is that the particular tests employed must be compatible.

This completely automatable technology for screening biological samples and comparing their unique DNA marker profiles permits rapid and efficient identification of individual biomolecules whose presence, absence or altered expression can be or is associated with a disease or condition of interest. Thus, in its simplest form, the present invention provides a method and an apparatus for analyzing a biological sample for the presence of a disease condition and/or disease predisposition and/or infectious agent and simultaneously determining the DNA fingerprint or genotype of the biological sample so as to provide internal identification of the biological sample.

5.1. Methods of Determining the Molecular Barcode of a Subject

In general, DNA fingerprinting or DNA typing for the determination of one's molecular barcode, as well as other methods of genotyping, profiling and DNA identification analysis, refer to the characterization of either similarities or one or more distinctive features in the genetic make up or genome of an individual, a variety or race, or a species. The general rule is that the closer the genetic relationship is, the greater the identity or more appropriate the similarity of genomes, and consequently distinctive features in the genome will be rarer. These similar or distinctive features can be revealed by analyzing the DNA of an organism after cleaving the DNA with a restriction endonuclease. Because of their high degree of sequence specificity, restriction endonucleases will cleave DNA molecules in a very specific fashion. The result is that a reproducible set of DNA fragments will be produced. DNA fragments can be fractionated according to their length on porous matrices, or gels, yielding typical banding patterns, which constitutes a DNA fingerprint or molecular barcode of the organism's genetic makeup.

When the fingerprints of very closely related species, varieties or races are compared, the DNA fingerprints can be identical or very similar. When differences are observed within otherwise identical DNA fingerprints, such differences are referred to as DNA polymorphisms: these are new DNA fragments which appear in a DNA fingerprint. The DNA is said to be polymorphic at that position and the novel DNA fragment can be used as a DNA marker. DNA polymorphisms detected in DNA fingerprints obtained by restriction enzyme cleavage can result from any of the following alterations in the DNA sequence: mutations abolishing the restriction endonuclease target site, mutations creating new target sites, insertions, deletions or inversions between the two restriction sites.

Such DNA polymorphisms are generally referred to as Restriction Fragment Length Polymorphisms or RFLPs. Such mutational changes will behave as bona fide genetic markers when they are inherited in a mendelian fashion. Consequently, DNA polymorphisms can be used as genetic markers in much the same way as other genetic markers: in parentage analysis, in genetic studies on the inheritance of traits, or in the identification of individuals.

In accordance with the present invention, the terms genotyping, fingerprinting, and DNA typing are meant to include the use of any means known to those skilled in the art for determining an individual's genotype molecular barcode. For example, and without limitation, and as will be explained in more detail below, techniques for genotyping can be nucleic acid based including size fractionation, allele specific oligonucleotide (ASO) hybridization, sequencing, restriction fragment length polymorphism (RFLP) analysis, denaturation temperature analysis, mass spectrometry analysis, etc. The genetic typing may be performed on genomic DNA, mitochondrial DNA or may be based on typing the RNA present in a cell. See e.g., Zang Y. H. & McCabe E. R., RNA Analysis from Newborn Screening Dried Blood Specimens, *Hum. Genet.* (1992) 89(3): 311-4. Further, the typing methodology may be any that is currently used in the art, including techniques that are sequence based, size analysis based, hybridization based or a combination thereof. Generally, DNA samples nay be amplified before analysis in a PCR or PCR-like reaction. Genetic typing methodologies are well known to those of ordinary skill in the art.

DNA fingerprinting to determine one's molecular barcode as used in the context of the present invention is therefore a broad term used to designate methods for assessing sequence differences in DNA isolated from various sources, e.g., by comparing the presence of marker DNA in samples of isolated DNA. Typically, DNA fingerprinting is used to analyze and compare DNA from different species of organisms or DNA from different individuals of the same species. DNA sequence differences detected by fingerprinting are referred to as DNA polymorphisms. The presence of a DNA polymorphism in an organism's DNA can serve to indicate that the genetic origin of such an organism is different from the genetic origin of organisms whose DNA does not have the polymorphism. Such DNA polymorphisms can result, e.g., from insertion, deletion, and/or mutation events in the genome.

Thus, in accordance with one embodiment of the present invention there is provided a method for identification of a biological sample of a mammal, which comprises the steps of:

a) obtaining a genomic DNA sample from said mammal;

b) performing amplification of the genomic DNA sample using at least two primers for amplification of at least two DNA markers; and c) identifying the amplified DNA markers from step b), wherein the genomic DNA sample's unique combination of amplified markers represents the molecular barcode for identification of the biological sample.

In accordance with a preferred embodiment of the present invention there is provided a method for identification of a biological sample of a mammal, which comprises the steps of:

a) obtaining a genomic DNA sample from said mammal;

b) performing DNA amplification of the genomic DNA sample using at least two primers for amplification of at least two DNA markers, wherein said DNA marker amplification primers are selected from the group consisting of the following primer pairs:

```
D3S1358
5' Primer
ACTGCAGTCCAATCTGGGT            (SEQ ID NO: 1)

3' primer
ATGAAATCAACAGAGGCTTG;          (SEQ ID NO: 2)

D5S818
5' Primer
GGGTGATTTTCCTCTTTGGT           (SEQ ID NO: 3)

3' primer
TGATTCCAATCATAGCCACA;          (SEQ ID NO: 4)

D7S820
5' Primer
TGTCATAGTTTAGAACGAACTAACG      (SEQ ID NO: 5)

3' primer
GTGAGGTATCAAAAACTCAGAGG;       (SEQ ID NO: 6)

D13S317
5' Primer
ACAGAAGTCTGGGATGTGGA           (SEQ ID NO: 7)

3' primer
GCCCAAAAAGACAGACAGAA;          (SEQ ID NO: 8)
and

D16S539
5' Primer
GATCCCAAGCTCTTCCTCTT           (SEQ ID NO: 9)

3' primer
ACGTTTGTGTGTGCATCTGT;          (SEQ ID NO: 10)
and
``` complementary sequences thereto; and c) identifying the amplified DNA markers from step b), wherein the genomic DNA sample's unique combination of amplified markers represents the molecular barcode for identification of the biological sample.

In accordance with the present invention, any genetic-marker technologies are adaptable to the determination of one's molecular barcode, including restriction-fragment-length polymorphism (RFLP) Bostein et at (1980) Am J Hum Genet 32:314-331; single strand conformation polymorphism (SSCP) Fischer et al. (1983) Proc Natl Acad Sci USA 80:1579-1583; Orita et al. (1989) Genomics 5:874-879; amplified fragment-length polymorphism (AFLP) Vos et al. (1995) Nucleic Acids Res 23:4407-4414; microsatellite or single-sequence repeat (SSR) Weber J L and May P E (1989) Am J Hum Genet 44:388-396; rapid-amplified polymorphic DNA (RAPD) Williams et al (1990) Nucleic Acids Res 18:6531-6535; sequence tagged site (STS) Olson et al. (1989) Science 245:1434-1435; genetic-bit analysis (GBA) Nikiforov et al (1994) Nucleic Acids Res 22:4167-4175 (the entire contents of which are incorporated by reference in its entirety); allele-specific polymerase chain reaction (AS-PCR) Gibbs et al. (1989) Nucleic Acids Res 17:2437-2448, Newton et al. (1989) Nucleic Acids Res 17:2503-2516; nick-translation PCR (e.g., TaqMan™) Lee et al. (1993) Nucleic Acids Res 21:3761-3766; and allele-specific hybridization (ASH) Wallace et al. (1979) Nucleic Acids Res 6:3543-3557, Sheldon et al. (1993) Clinical Chemistry 39(4):718-719 (the entire contents of each of which are hereby incorporated by reference in their entirety). Kits for RAPD and AFLP analyses are commercially available, e.g., from Perkin Elmer Applied Biosystems (Foster City, Calif.). For example, the restriction fragment length polymorphism (RFLP) technique employs restriction enzyme digestion of DNA, followed by size separation of the digested DNA by gel electrophoresis, and hybridization of the size-separated DNA with a specific polynucleotide fragment. Differences in the size of the restriction fragments to which the polynucleotide probe binds reflect sequence differences in DNA samples, or DNA polymorphisms. See Tanksley, Biotechnology 7:257-264 (1988).

5.2. Methods of Diagnosis of a Subject

In accordance with the present invention, the particular methods that can be employed for the diagnosis of a subject to determine whether a subject is afflicted with a particular disease or disorder, or is at risk of developing a particular disorder, the existence of genetic lesions or mutations can be detected by, for example, but not limited to, ascertaining the existence of at least one of: 1) a deletion of one or more nucleotides from a given gene; 2) an addition of one or more nucleotides to a given gene; 3) a substitution of one or more nucleotides of a given gene; 4) a chromosomal rearrangement of a given gene; 5) an alteration in the level of a messenger RNA transcript of a given gene; 6) an aberrant modification of a given gene, such as of the methylation pattern of the genomic DNA; 7) the presence of a non-wild type splicing pattern of a messenger RNA transcript of a given gene; 8) a non-wild type level of a the protein encoded by a given gene; 9) an allelic loss of a given gene; and 10) an inappropriate post-translational modification of the protein encoded by a given gene. As described herein, there are a large number of assay techniques known in the art which can be used for detecting lesions in a given gene.

For example, in certain embodiments of the invention, detection of a genetic lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1994) Proc. Natl. Acad. Sci. USA 91:360-364), the latter of which can be particularly useful for detecting point mutations in a given gene (see, e.g., Abravaya et al. (1995) Nucleic Acids Res. 23:675-682) (the entire contents of each of which are hereby incorporated by reference in their entirety). This method can include the steps of collecting a sample of cells from a patient, isolating nucleic acid (e.g., genomic, mRNA or both) from the cells of the sample, contacting the nucleic acid sample with one or more primers which specifically hybridize to the selected gene under conditions such that hybridization and amplification of the gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

In certain embodiments of the invention, alternative amplification methods include, but are not limited to, self sustained sequence replication (Guatelli et al. (1990) Proc. Natl. Acad. Sci. USA 87:1874-1878), transcriptional amplification system (Kwoh, et al. (1989) Proc. Natl. Acad. Sci. USA 86:1173-1177), Q-Beta Replicase (Lizardi et al. (1988) Bio/Technology 6:1197) (the entire contents of each of which are hereby incorporated by reference in their entirety), or any other nucleic acid amplification method, followed by the detection of the amplified molecules using techniques well known to those of skill in the art. These detection schemes are especially useful for the detection of nucleic acid molecules if such molecules are present in very low copy numbers.

In another embodiment of the present invention, mutations in a selected gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,498,531) can be used to score for the presence of specific mutations by development or loss of a ribozyme cleavage site.

In other embodiments of the present invention, genetic mutations can be identified by hybridizing a sample and control nucleic acids, e.g., DNA or RNA, to high density arrays containing hundreds or thousands of oligonucleotides probes (Cronin et al. (1996) *Human Mutation* 7:244-255; Kozal et al. (1996) *Nature Medicine* 2:753-759) (the entire contents of each of which are hereby incorporated by reference in their entirety). The use of automated scoring techniques and sophisticated data analysis software permits the collection of large amounts of data very quickly. (see e.g., U.S. Pat. No. 5,827,482; U.S. Pat. No. 5,821,060; U.S. Pat. No. 5,795,716; U.S. Pat. No. 5,763,599; U.S. Pat. No. 5,741,644; U.S. Pat. No. 5,733,729; U.S. Pat. No. 5,733,509; U.S. Pat. No. 5,731,152; U.S. Pat. No. 5,728,532; U.S. Pat. No. 5,671,303; U.S. Pat. No. 5,632,957; U.S. Pat. No. 5,605,662; U.S. Pat. No. 5,599,668; U.S. Pat. No. 5,593,839; U.S. Pat. No. 5,571,639; U.S. Pat. No. 5,561,071; and U.S. Pat. No. 5,445,934 (the entire contents of each of which are herein incorporated by reference in their entirety). See also; Wang D. G., et al., Large-scale identification, mapping, and genotyping of single-nucleotide polymorphisms in the human genome, *Science* (1998) 280 (5366): 1077-82; Hacia J. G., et al., Evolutionary sequence comparisons using high-density oligonucleotide arrays, *Nat. Genet.* (1998) 18(2): 155-8; Livache T., et al., Polypyrrole DNA chip on a silicon device: example of hepatitis C virus genotyping, *Anal. Biochem.* (1998) 255 (2): 188-94; Pastinen T., et al., Minisequencing: a specific tool for DNA analysis and diagnostics on oligonucleotide arrays, *Genome Res.* (1997) 7(6): 606-14; Wang J., et al., Nucleic-acid immobilization, recognition and detection at chronopotentiometric DNA chips, *Biosens. Bioelectron.* (1997) 12 (7): 587-99; Hacia J. G., et al., Detection of heterozygous mutations in BRCA1 using high density oligonucleotide arrays and two-colour fluorescence analysis, *Nat. Genet.* (11996) 14(4): 441-7; Schena M., et al., Parallel human genome analysis: microarray-based expression monitoring of 1000 genes, *Proc. Natl. Acad. Sci. USA* (1996) 93(20): 10614-9; Southern E. M., DNA chips: analysing sequence by hybridization to oligonucleotides on a large scale, *Trends Genet.* (1996) 12(3): 110-5; Stimpson D. I., et al., Real-time detection of DNA hybridization and melting on oligonucleotide arrays by using optical wave guides, *Proc. Natl. Acad. Sci. USA* (1995) 92(14): 6379-83; Pease A. C., et al., Light-generated oligonucleotide arrays for rapid DNA sequence analysis, *Proc. Natl. Acad. Sci. USA* (1994) 91(11): 5022-6; Shumaker et al., Mutation Detection by Solid Phase Primer Extension, *Hum. Mutation* (1996) 7:346-54 (the entire contents of each of which are hereby incorporated by reference in their entirety).

For example, and not by way of limitation, genetic mutations can be identified in two-dimensional arrays containing light-generated DNA probes as described in Cronin et al., supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment of the present invention, any of a variety of sequencing reactions known in the art can be used to directly sequence a given gene and detect mutations by comparing the sequence of the sample nucleic acids with the corresponding wild-type (control) sequence. Examples of sequencing reactions include those based on techniques developed by Maxim and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Bio/Techniques* 19:448), including sequencing by mass spectrometry (see, e.g., PCT Publication No. WO 94/16101; Cohen et al. (1996) *Adv. Chromatogr.* 36:127-162; and Griffin et al. (1993) *Appl. Biochem. Biotechnol.* 38:147-159) (the entire contents of each of which are hereby incorporated by reference in their entirety).

Other methods encompassed within the present invention for detecting mutations in a selected gene include those methods in which protection from cleavage agents is used to detect mismatched bases in RNA/RNA or RNA/DNA heteroduplexes (Myers et al. (1985) *Science* 230:1242). In general, the technique of mismatch cleavage entails providing heteroduplexes formed by hybridizing (labeled) RNA or DNA containing the wild-type sequence with potentially mutant RNA or DNA obtained from a tissue sample. The double-stranded duplexes are treated with an agent which cleaves single-stranded regions of the duplex such as which will exist due to base pair mismatches between the control and sample strands. RNA/DNA duplexes can be treated with RNase to digest mismatched regions, and DNA/DNA hybrids can be treated with S1 nuclease to digest mismatched regions.

In other embodiments of the present invention, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, e.g., Cotton et al. (1988) *Proc. Natl. Acad. Sci. USA* 85:4397; Saleeba et al. (1992) *Methods Enzymol.* 217:286-295 (the entire contents of each of which are hereby incorporated by reference in their entirety). In a preferred embodiment, the control DNA or RNA can be labeled for detection.

In still another embodiment of the present invention, the mismatch cleavage reaction employs one or more proteins that recognize mismatched base pairs in double-stranded DNA (so called DNA mismatch repair enzymes) in defined systems for detecting and mapping point mutations in cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662) (the entire contents of which are hereby incorporated by reference in their entirety). According to an exemplary embodiment, a probe based on a selected sequence, e.g., a wild-type sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments of the present invention, alterations in electrophoretic mobility will be used to identify mutations in genes. For example, single strand conformation polymorphism (SSCP) may be used to detect differences in electrophoretic mobility between mutant and wild type nucleic acids (Orita et al. (1989) *Proc. Natl. Acad. Sci. USA* 86:2766; see also Cotton (1993) *Mutat. Res.* 285:125-144; Hayashi (1992) *Genet. Anal. Tech. Appl* 9:73-79) (the entire contents of each of which are hereby incorporated by reference in their entirety). Single-stranded DNA fragments of sample and control nucleic acids will be denatured and allowed to renature. The secondary structure of single-stranded nucleic acids varies according to sequence, and the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet.* 7:5) (the entire contents of which are hereby incorporated by reference in their entirety).

In yet another embodiment of the method of the present invention, the movement of mutant or wild-type fragments in polyacrylamide gels containing a gradient of denaturant is assayed using denaturing gradient gel electrophoresis (DGGE) (Myers et al. (1985) *Nature* 313:495) (the entire contents of which are hereby incorporated by reference in their entirety). When DGGE is used as the method of analysis, DNA will be modified to insure that it does not completely denature, for example by adding a 'GC clamp of approximately 40 bp of high-melting GC-rich DNA by PCR. In a further embodiment of the present invention, a temperature gradient is used in place of a denaturing gradient to identify differences in the mobility of control and sample DNA (Rosenbaum and Reissner (1987) *Biophys. Chem.* 265:12753) (the entire contents of which are hereby incorporated by reference in their entirety).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl. Acad. Sci. USA* 86:6230) (the entire contents of each of which are hereby incorporated by reference in their entirety). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the method of the instant invention. Oligonucleotides used as primers for specific amplification may carry the mutation of interest in the center of the molecule (so that amplification depends on differential hybridization) (Gibbs et al. (1989) *Nucleic Acids Res.* 17:2437-2448) (the entire contents of which are hereby incorporated by reference in their entirety) or at the extreme 3' end of one primer where, under appropriate conditions, mismatch can prevent or reduce polymerase extension (Prossner (1993) *Tibtech* 11:238) (the entire contents of which are hereby incorporated by reference in their entirety).

In addition, it may be desirable to introduce a novel restriction site in the region of the mutation to create cleavage-based detection (Gasparini et al. (1992) *Mol. Cell Probes* 6:1) (the entire contents of which are hereby incorporated by reference in their entirety). It is anticipated that in certain embodiments of the present invention amplification may also be performed using Taq ligase for amplification (Barany (1991) *Proc. Natl. Acad. Sci. USA* 88:189) (the entire contents of which are hereby incorporated by reference in their entirety). In such cases, ligation will occur only if there is a perfect match at the 3' end of the 5' sequence making it possible to detect the presence of a known mutation at a specific site by looking for the presence or absence of amplification.

Yet another means of analyzing genetic information is "dynamic allele specific hybridization" (DASH). This technique uses labeled oligonucleotides in a multiwell format that will fluoresce when the oligonucleotide exists in a double-stranded form, but not when it is single-stranded. Adding a single strand of the DNA to be tested allows the strands to hybridize. The temperature at which the strands again denature will allow identification of the base at the SNP. This technique has the advantage that it is technically simple, not requiring expensive detection devices, such as mass spectrometers. Furthermore, it is expected that DNA sequencing and genotyping methodology will continue to evolve and will present additional viable means of quickly genotyping an individual. See e.g., Xu L., et al., Electrophore mass tag dideoxy DNA sequencing, *Anal. Chem.* (1997) 69(17): 3595-602, Haff L. A., Smirnov I. P., Single-nucleotide polymorphism identification assays using a thermostable DNA polymerase and delayed extraction MALDI-TOF mass spectrometry, *Genome Res.* (1997) 7(4): 378-88; Taranenko N. I., et al., Laser desorption mass spectrometry for point mutation detection, *Genet. Anal.* (1996) 13(4): 87-94; Tang K., et al., Matrix-assisted laser desorption/ionization mass spectrometry of immobilized duplex DNA probes, *Nucleic Acids Res.* (1995) 23(16): 3126-31; Griffin H. G. & Griffin A. M., DNA sequencing. Recent innovations and future trends, *Appl. Biochem. Biotechnol.* (1993) 38 (1-2): 147-59; Fauser S. & Wissinger B., Simultaneous detection of multiple point mutations using fluorescence-coupled competitive primer extension, *Biotechniques* (1997) 22(5): 964-8; Fox S. A., et al., Rapid genotyping of hepatitis C virus isolates by dideoxy fingerprinting, *J. Virol. Methods* (1995) 53(1): 1-9 (the entire contents of each of which are hereby incorporated by reference in their entirety).

In certain embodiments of the method of the present invention, any array of markers with a reasonably high probability of individualization is sufficient for these purposes. The markers can be Variable Number Tandem Repeats (VNTRs), short tandem repeats (STRs), CTRs, SNPs, microsatellites, etc. The number of markers that can be used herein is virtually limitless and the reader is referred to GENBANK and the literature for identification of markers which have been successfully used in genotyping methodologies. In the case of STRs, variable numbers of STRs may be used in the methods of the invention. For example, from two to thirteen different STR markers may be employed. A more preferred range of STR markers would be from about five to about ten STR markers. The most preferred would be at least five STR markers By way of example, and not by way of limitation, representative examples of STRs that may be used in the methods of the present invention include those which the Federal Bureau of Investigation (FBI) use in the identification of perpetrators of violent crime. For example, In 1997, the FBI announced the selection of 13 STR loci to constitute the core of the United States national database, CODIS. All CODIS STRs are tetrameric repeat sequences.

| | Locus | | | | | | |
|---|---|---|---|---|---|---|---|
| | D3S1358 | vWA | FGA | D8S1179 | D21S11 | D18S51 | D5S818 |
| Genotype | 15, 18 | 16, 16 | 19, 24 | 12, 13 | 29, 31 | 12, 13 | 11, 13 |
| Frequency | 8.2% | 4.4% | 1.7% | 9.9% | 2.3% | 4.3% | 13% |

| | Locus | | | | | | |
|---|---|---|---|---|---|---|---|
| Locus | D13S317 | D7S820 | D16S539 | THO1 | TPOX | CSF1PO | AMEL |
| Genotype | 11, 11 | 10, 10 | 11, 11 | 9, 9.3 | 8, 8 | 11, 11 | X Y |
| Frequency | 1.2% | 6.3% | 9.5% | 9.6% | 3.52% | 7.2% | (Male) |

The primers and oligonucleotides contemplated for use in the methods of the present invention are preferably DNA, and can be synthesized using standard techniques and, when appropriate, detectably labeled using standard methods (Ausubel et al., supra). Detectable labels that can be used to tag the primers and oligonucleotides used in the methods of the invention include, but are not limited to, digoxigenin, fluorescent labels (e.g., fluorescein and rhodamine), enzymes (e.g., horseradish peroxidase and alkaline phosphatase), biotin (which can be detected by anti-biotin specific antibodies or enzyme-conjugated avidin derivatives), radioactive labels (e.g., $^{32}P$ and $^{125}I$), calorimetric reagents, and chemiluminescent reagents. The labels used in the methods of the invention are detected using standard methods.

The specific binding pairs useful in the methods of the invention include, but are not limited to, avidin-biotin, streptavidin-biotin, hybridizing nucleic acid pairs, interacting protein pairs, antibody-antigen pairs, reagents containing chemically reactive groups (e.g., reactive amino groups), and nucleic acid sequence-nucleic acid binding protein pairs.

The solid supports useful in the methods of the invention include, but are not limited to, agarose, acrylamide, and polystyrene beads; polystyrene microtiter plates (for use in, e.g., ELISA); and nylon and nitrocellulose membranes (for use in, e.g., dot or slot blot assays).

Some methods of the invention employ solid supports containing arrays of nucleic acid probes. In these cases, solid supports made of materials such as glass (e.g., glass plates), silicon or silicon-glass (e.g., microchips), or gold (e.g., gold plates) can be used. Methods for attaching nucleic acid probes to precise regions on such solid surfaces, e.g., photolithographic methods, are well known in the art, and can be used to make solid supports for use in the invention. (For example, see, Schena et al., Science 270:467-470, 1995; Kozal et al., Nature Medicine 2(7):753-759, 1996; Cheng et al., Nucleic Acids Research 24(2):380-385, 1996; Lipshutz et al., BioTechniques 19(3):442-447, 1995; Pease et al., Proc. Natl. Acad. Sci. USA 91:5022-5026, 1994; Fodor et al., Nature 364:555-556, 1993; Pirrung et al., U.S. Pat. No. 5,143,854; and Fodor et al., WO 92/10092.) (the entire contents of each of which are hereby incorporated by reference in their entirety).

Thus, in accordance with one aspect of the present invention a method is provided for the diagnosis of a subject to determine whether a subject is afflicted with a particular disease or disorder, or is at risk of developing a particular disorder, coupled with the identification of the molecular barcode of the biological sample, wherein the result obtained from the diagnosis is thereby intimately associated with the unique molecular barcode of the sample of the subject being diagnosed.

Thus, in accordance with yet another preferred embodiment, a method is provided for the diagnosis of a subject to determine whether a subject is afflicted with a particular disease or disorder, or is at risk of developing a particular disorder, coupled with the identification of the molecular barcode of the biological sample by VNTR analysis, wherein the result obtained from the diagnosis is thereby intimately associated with the molecular barcode of the sample of the subject being diagnosed.

In accordance with yet another preferred embodiment, a method is provided for the diagnosis of a subject to determine whether a subject is afflicted with a particular disease or disorder, or is at risk of developing a particular disorder, coupled with the identification of the molecular barcode of the biological sample by STR analysis, wherein the result obtained from the diagnosis is thereby intimately associated with the molecular barcode of the sample of the subject being diagnosed.

In accordance with yet another preferred embodiment, a method is provided for the diagnosis of a subject to determine whether a subject is afflicted with a particular disease or disorder, or is at risk of developing a particular disorder, coupled with the identification of the molecular barcode of the biological sample by CTR analysis, wherein the result obtained from the diagnosis is thereby intimately associated with the molecular barcode of the sample of the subject being diagnosed.

In accordance with yet another preferred embodiment, a method is provided for the diagnosis of a subject to determine whether a subject is afflicted with a particular disease or disorder, or is at risk of developing a particular disorder, coupled with the identification of the molecular barcode of the biological sample by SNP analysis, wherein the result obtained from the diagnosis is thereby intimately associated with the molecular barcode of the sample of the subject being diagnosed.

In accordance with yet another preferred embodiment, a method is provided for the diagnosis of a subject to determine whether a subject is afflicted with a particular disease or disorder, or is at risk of developing a particular disorder, coupled with the identification of the molecular barcode of the biological sample by microsatellite analysis, wherein the result obtained from the diagnosis is thereby intimately associated with the molecular barcode of the sample of the subject being diagnosed.

In certain preferred embodiments, the diagnosis is for the purposes of, but not limited to, paternity, genetic screening, prenatal diagnosis, presymptomatic diagnosis, carrier detection, and/or forensic chemical analysis.

Thus, in one embodiment of the present invention, a method is provided for identification of a biological sample of a subject undergoing diagnosis to determine whether the subject is afflicted with a particular disease or disorder, or is at risk of developing a particular disorder comprising a) obtaining a genomic DNA sample from a subject;

b) performing DNA amplification of the genomic DNA sample using at least two primers for amplification of at least two DNA markers;

c) identifying the amplified DNA markers of step b), wherein the genomic DNA sample's unique combination of amplified markers represents the molecular barcode for identification of the biological sample; and d) performing diagnosis of the subject's genomic DNA sample to determine whether the subject is afflicted with a particular disease or disorder, or is at risk of developing a particular disease or disorder, wherein the result obtained from said diagnosis step is intimately associated with the molecular barcode of the sample of the subject being diagnosed.

In yet another preferred embodiment of the present invention, a method is provided for identification of a biological sample of a subject undergoing diagnosis to determine whether the subject is afflicted with a particular disease or disorder, or is at risk of developing a particular disorder comprising a) obtaining a genomic DNA sample from a subject;

b) performing DNA amplification of the genomic DNA sample using at least two primers for amplification of at least two DNA markers wherein said DNA marker amplification primers are selected from the group consisting of the following primer pairs:

```
D3S1358
5' Primer
ACTGCAGTCCAATCTGGGT            (SEQ ID NO: 1)

3' primer
ATGAAATCAACAGAGGCTTG;          (SEQ ID NO: 2)

D5S818
5' Primer
GGGTGATTTTCCTCTTTGGT           (SEQ ID NO: 3)

3' primer
TGATTCCAATCATAGCCACA;          (SEQ ID NO: 4)

D7S820
5' Primer
TGTCATAGTTTAGAACGAACTAACG      (SEQ ID NO: 5)

3' primer
CTGAGGTATCAAAAACTCAGAGG;       (SEQ ID NO: 6)

D13S317
5' Primer
ACAGAAGTCTGGGATGTGGA           (SEQ ID NO: 7)

3' primer
GCCCAAAAAGACAGACAGAA;          (SEQ ID NO: 8)
and

D16S539
5' Primer
GATCCCAAGCTCTTCCTCTT           (SEQ ID NO: 9)

3' primer
ACGTTTGTGTGTGCATCTGT;          (SEQ ID NO: 10)
and
``` complementary sequences thereto;

c) identifying the amplified DNA markers of step b), wherein the genomic DNA sample's unique combination of amplified markers represents the molecular barcode for identification of the biological sample; and d) performing diagnosis of the subject's genomic DNA sample to determine whether the subject is afflicted with a particular disease or disorder, or is at risk of developing a particular disease or disorder, wherein the result obtained from said diagnosis step is thereby intimately associated with the molecular barcode of the sample of the subject being diagnosed.

In accordance with yet another embodiment of the present invention, the method of the invention can also be used to detect genetic lesions or mutations, thereby determining if a subject with the lesioned gene is at risk for a disorder characterized aberrant expression or activity of a given polypeptide, coupled with the identification of the molecular barcode of the biological sample, wherein the result obtained from the diagnosis is thereby intimately associated with the molecular barcode of the sample of the subject being diagnosed.

In yet another embodiment of the present invention, a method is provided for identification of a biological sample of a subject undergoing screening for genetic lesions or mutations to determine if the subject with a lesioned gene is at risk for a disease or disorder characterized by aberrant expression or activity of a given polypeptide comprising a) obtaining a genomic DNA sample from a subject;

b) performing DNA amplification of the genomic DNA sample using at least two primers for amplification of at least two DNA markers;

c) identifying the amplified DNA markers of step b), wherein the genomic DNA sample's unique combination of amplified markers represents the molecular barcode for identification of the biological sample; and d) performing screening of the subject's genomic DNA sample for detection of genetic lesions or mutations in said genomic DNA sample to determine if a subject with a lesioned gene is at risk for a disease or disorder characterized by aberrant expression or activity of a given polypeptide; wherein the result obtained from said screening step is thereby intimately associated with the molecular barcode of the sample of the subject being screened.

In yet another embodiment of the present invention, a method is provided for identification of a biological sample of a subject undergoing screening for genetic lesions or mutations to determine if the subject with a lesioned gene is at risk for a disease or disorder characterized by aberrant expression or activity of a given polypeptide comprising a) obtaining a genomic DNA sample from a subject;

b) performing DNA amplification of the genomic DNA sample using at least two primers for amplification of at least two DNA markers wherein said DNA marker amplification primers are selected from the group consisting of the following primer pairs:

```
D3S1358
5' Primer
ACTGCAGTCCAATCTGGGT            (SEQ ID NO: 1)

3' primer
ATGAAATCAACAGAGGCTTG;          (SEQ ID NO: 2)

D5S818
5' Primer
GGGTGATTTTCCTCTTTGGT           (SEQ ID NO: 3)

3' primer
TGATTCCAATCATAGCCACA;          (SEQ ID NO: 4)
```

```
D7S820
5' Primer
TGTCATAGTTTAGAACGAACTAACG    (SEQ ID NO: 5)

3' primer
CTGAGGTATCAAAAACTCAGAGG;     (SEQ ID NO: 6)

D13S317
5' Primer
ACAGAAGTCTGGGATGTGGA         (SEQ ID NO: 7)

3' primer
GCCCAAAAAGACAGACAGAA;        (SEQ ID NO: 8)
and

D16S539
5' Primer
GATCCCAAGCTCTTCCTCTT         (SEQ ID NO: 9)

3' primer
ACGTTTGTGTGTGCATCTGT;        (SEQ ID NO: 10)
and
``` complementary sequences thereto;

c) identifying the amplified DNA markers of step b), wherein the genomic DNA sample's unique combination of amplified markers represents the molecular barcode for identification of the biological sample;

d) performing screening of the subject's genomic DNA sample for detection of genetic lesions or mutations in said genomic DNA sample to determine if a subject with a lesioned gene is at risk for a disease or disorder characterized by aberrant expression or activity of a given polypeptide; wherein the result obtained from said screening step is intimately associated with the molecular barcode of the sample of the subject being screened.

In accordance with yet another preferred embodiment, the method of the present invention includes diagnosing, in a sample of cells from a subject, the presence or absence of a genetic lesion or mutation characterized by at least one of an alteration affecting the integrity of a gene encoding a given polypeptide, or the mis-expression of a gene encoding a given polypeptide, coupled with the simultaneous identification of the molecular barcode of the sample, wherein the result obtained from said diagnosis is intimately associated with the molecular barcode of the sample of the subject being diagnosed.

5.3. Methods of Diagnosis of a Subject to Detect the Presence of a Target Microorganism In addition to the identification of samples of subjects undergoing paternity screening, genetic screening, prenatal diagnosis, presymptomatic diagnosis, disease carrier detection, or forensic chemical analysis, the methods of the present invention also have application in methods of identifying samples of subjects undergoing diagnosis to determine the presence or absence of microorganisms.

In this aspect of the present invention, the target microorganism may include, for example, without limitation, virus, bacteria, fungi or protozoa or any combination thereof. Specific examples of bacteria to which the methods of the invention can be suitably applied include bacteria such as, for example, without limitation, *Mycobacteria tuberculosis*, *Rickettsia rickettsii*, *Ehrlichia chaffeensis*, *Borrelia burgdorferi*, *Yersinia pestis*, *Treponema pallidum*, *Chlamydia trachomatis*, *Chlamydia pneumoniae*, *Mycoplasma pneumoniae*, *Mycoplasma* sp., *Legionella pneumophila*, *Legionella dumoffii*, *Mycoplasma fermentans*, *Ehrlichia* sp., *Haemophilus influenzae*, *Neisseria meningitidis*, *Streptococcus pneumonia*, *S. agalactiae*, and *Listeria monocytogenes*. Specific examples of viruses to which the methods of the invention can be suitably applied include viruses such as, for example, without limitation, Human Immunodeficiency Virus Type 1 (HIV-1), Human T-Cell Lymphotrophic Virus Type 1 (HTLV-1), Hepatitis B Virus (HBV), Hepatitis C Virus (HCV), Herpes Simplex, Herpesvirus 6, Herpesvirus 7, Epstein-Barr Virus, Cytomegalovirus, Varicella-Zoster Virus, JC Virus, Parvovirus B19, Influenza A, B and C, Rotavirus, Human Adenovirus, Rubella Virus, Human Enteroviruses, Genital Human Papillomavirus (HPV), and Hantavirus. Specific examples of fingi to which the methods of the invention can be suitably applied include fungi such as, for example, without limitation, *Cryptococcus neoformans*, *Pneumocystis carinii*, *Histoplasma capsulatum*, *Blastomyces dermatitidis*, *Coccidioides immitis*, and *Trichophyton rubrum*. Specific examples of protozoa to which the methods of the invention can be suitably applied include protozoa such as, for example, without limitation, *Trypanosoma cruzi*, *Leishmania* sp., *Plasmodium*, *Entamoeba histolytica*, *Babesia microti*, *Giardia lamblia*, *Cyclospora* sp. and *Eimeria sp.*

Thus, in accordance with one embodiment of the present invention, a method is provided for the diagnosis of a subject to detect the presence of a target microorganism, coupled with the simultaneous identification of the molecular barcode of a biological sample, wherein the result obtained from the diagnosis is intimately associated with the molecular barcode of the sample of the subject being diagnosed.

In yet another embodiment of the present invention, a method is provided for identification of a biological sample of a subject being diagnosed for the presence of a target microorganism comprising the steps of a) obtaining a genomic DNA sample from a subject;

b) performing DNA amplification of the genomic DNA sample using at least two primers for amplification of at least two DNA markers; and c) identifying the amplified DNA markers of step b), wherein the genomic DNA sample's unique combination of amplified markers represents the molecular barcode for identification of the biological sample; and d) performing diagnosis of said subject to detect the presence of a target microorganism; wherein the result obtained from said diagnosis step is intimately associated with the molecular barcode of the sample of the subject being diagnosed.

In yet another preferred embodiment of the present invention, a method is provided for identification of a biological sample of a subject being diagnosed for the presence of a target microorganism comprising the steps of a) obtaining a genomic DNA sample from a subject;

b) performing DNA amplification of the genomic DNA sample using at least two primers for amplification of at least two DNA markers wherein said DNA marker amplification primers are selected from the group consisting of the following primer pairs:

```
D3S1358
5' Primer
ACTGCAGTCCAATCTGGGT          (SEQ ID NO: 1)

3' primer
ATGAAATCAACAGAGGCTTG;        (SEQ ID NO: 2)

D5S818
5' Primer
GGGTGATTTTCCTCTTTGGT         (SEQ ID NO: 3)
```

```
                    -continued
3' primer
TGATTCCAATCATAGCCACA;        (SEQ ID NO: 4)

D7S820
5' Primer
TGTCATAGTTTAGAACGAACTAACG    (SEQ ID NO: 5)

3' primer
CTGAGGTATCAAAAACTCAGAGG;     (SEQ ID NO: 6)

D13S317
5' Primer
ACAGAAGTCTGGGATGTGGA         (SEQ ID NO: 7)

3' primer
GCCCAAAAAGACAGACAGAA;        (SEQ ID NO: 8)
and

D16S539
5' Primer
GATCCCAAGCTCTTCCTCTT         (SEQ ID NO: 9)

3' primer
ACGTTTGTGTGTGCATCTGT;        (SEQ ID NO: 10)
and
``` complementary sequences thereto; and c) identifying the amplified DNA markers of step b), wherein the genomic DNA sample's unique combination of amplified markers represents the molecular barcode for identification of the biological sample; and d) performing diagnosis of said subject to detect the presence of a target microorganism; wherein the result obtained from said diagnosis step is intimately associated with the molecular barcode of the sample of the subject being diagnosed.

5.4. Biological Samples

As used herein, it is intended that the term "patient sample" or "biological sample" refers to any solid or fluid sample obtained from, excreted by or secreted by any living organism, including single-celled microorganisms (such as bacteria and yeasts) and multicellular organisms (such as plants and animals, for instance a vertebrate or a mammal, and in particular a healthy or apparently healthy human subject or a human patient affected by a condition or disease to be diagnosed or investigated).

A biological sample may be from a biological fluid obtained from any site (e.g. a tissue homogenate, hair, blood, semen, vaginal swab, plasma, serum, ascites, pleural effusion, thoracentesis sample, spinal fluid, lymph fluid, bone marrow, the external sections of the skin, respiratory, intestinal, and genito-urinary tracts, stool, urine, sputum, tears, saliva, mixtures of body fluids, vitreous humor, amniotic fluid, chorionic villus samples, blood cells, tumors, organs, tissue, and samples of in vitro cell culture constituents), a transudate, an exudate (e.g. fluid obtained from an abscess or any other site of infection or inflammation), or fluid obtained from a joint (e.g. a normal joint or a joint affected by disease such as for example, without limitation, rheumatoid arthritis, osteoarthritis, gout or septic arthritis).

Alternatively, a biological sample can be obtained from any organ or tissue (including a biopsy or autopsy specimen) or may comprise cells (whether primary cells or cultured cells) or medium conditioned by any cell, tissue or organ. If desired, the biological sample may be subjected to preliminary processing, including preliminary separation techniques. For example, cells or tissues can be extracted and subjected to subcellular fractionation for separate analysis of biomolecules in distinct subcellular fractions, e.g. proteins or drugs found in different parts of the cell. See Deutscher (ed.), 1990, Methods In Enzymology vol. 182, pp. 147-238 (incorporated herein by reference in its entirety).

By way of example, and not by way of limitation, in the analysis of whether a particular gene contains a mutation, most simply, blood can be drawn and DNA extracted from the cells of the blood. In addition, prenatal diagnosis can be accomplished by testing fetal cells, placental cells or amniotic cells for mutations of a given gene. Alteration of a wild-type gene allele, whether, for example, by point mutation or deletion, can be detected by any of the means discussed above. When the probes are used to detect the presence of the target sequences (for example, in screening for the presence of a particular disease, or susceptibility to a particular disorder, the biological sample to be analyzed, such as, for example, without limitation, blood, plasma, serum, ascites, pleural effusion, thoracentesis sample, spinal fluid, lymph fluid, bone marrow, the external sections of the skin, respiratory, intestinal, and genito-urinary tracts, stool, urine, sputum, tears, saliva, blood cells, tumors, organs, tissue and samples of in vitro cell culture constituents, may be treated, if desired, to extract the nucleic acids. Only a minute quantity of nucleic acid is required, and the nucleic acid can be either DNA or RNA (in the case of RNA, a reverse transcription step is required before the PCR step).

Thus, in accordance with the present invention, a "biological nucleic acid" is a nucleic acid (DNA, RNA, a combination thereof or an analogue thereof) which is isolated from a biological source or which is synthesized to have a nucleotide sequence which includes a region of sequence identity to a nucleic acid isolated from a biological source. Examples of biological nucleic acids are derived, e.g., from cDNA, genomic DNA isolated from an animal, genomic DNA isolated from an animal extract, genomic DNA isolated from an isolated animal tissue, genomic DNA isolated from an isolated animal tissue extract, genomic DNA isolated from an animal cell culture, genomic DNA isolated from an animal cell culture extract, genomic DNA isolated from a recombinant animal cell comprising a nucleic acid derived from an animal, genomic DNA isolated from an animal egg, genomic DNA isolated from an extract of a recombinant animal cell, and/or DNA isolated from a mitochondria.

Other examples of biological nucleic acids suitable for use in the methods of the present invention which involve the analysis of plant materials for the diagnosis of disease traits and/or for the detection of infectious agents are those biological nucleic acids derived, e.g., from genomic DNA isolated from a plant, genomic DNA isolated from a plant extract, genomic DNA isolated from an isolated plant tissue, genomic DNA isolated from an isolated plant tissue extract, genomic DNA isolated from a plant cell culture, genomic DNA isolated from a plant cell culture extract, genomic DNA isolated from a recombinant cell comprising a nucleic acid derived from a plant, genomic DNA isolated from a plant seed, genomic DNA isolated from an extract of a recombinant plant cell comprising a nucleic acid derived from a plant, and DNA isolated from a chloroplast. Certain types of sources are preferred, depending on the application. For example, plant tissues or seeds are preferred for performing selection of crops. Animal tissues are preferred for performing selection of animals. Methods of isolating DNAs from cells, organelles, tissues, homogenates and the like are well known in the art, as are methods of making cDNAs from isolated RNAs or cloned libraries.

5.5. Labeling and Detecting Probes

DNAs from biological samples for use in the methods of the present invention can be amplified and labeled in several ways, including, for example, and not by way of limitation, 1) Chemiluminescence [using both Horseradish Peroxidase and/or Alkaline Phosphatase with substrates that produce photons as breakdown products] [kits available from Amersham, Boehringer-Mannheim, and Life Technologies/Gibco BRL], 2) Color production [using both Horseradish Peroxidase and/or Alkaline Phosphatase with substrates that produce a colored precipitate] [kits available from Life Technologies/Gibco BRL, and Boehringer-Mannheim], 3) Chemifluorescence using Alkaline Phosphatase and the substrate AttoPhos [Amersham] or other substrates that produce fluorescent products, 4) Fluorescence [using Cy-5 [Amersham], fluorescein, and other fluorescent tags], 5) Radioactivity using end-labeling, nick translation, random priming, or PCR to incorporate radioactive molecules into the probe DNA/oligonucleotide. Other methods for labeling and detection will be readily apparent to one skilled in the art.

More generally, a probe for use in an in situ detection procedure, an in vitro amplification procedure (PCR, LCR, etc.), hybridization techniques (allele-specific hybridization, in situ analysis, Southern analysis, northern analysis, etc.) or any other detection procedure herein, can be labeled with any composition detectable by spectroscopic, photochemical, biochemical, immunochemical, electrical, optical or chemical means. Useful labels in the present invention include spectral labels such as fluorescent dyes (e.g., fluorescein isothiocyanate, Texas red, rhodamine, dixogenin, biotin, and the like), radiolabels (e.g., $^3$H, $^{125}$, $^{35}$S, $^{14}$C, $^{32}$P, $^{33}$P, etc.), enzymes (e.g., horse-radish peroxidase, alkaline phosphatase etc.) spectral calorimetric labels such as colloidal gold or colored glass or plastic (e.g. polystyrene, polypropylene, latex, etc.) beads. The label may be coupled directly or indirectly to a component of the detection assay employed in the methods (e.g., a probe, primer, isolated DNA, amplicon, YAC, BAC or the like) according to methods well known in the art. As indicated above, a wide variety of labels may be used, with the choice of label depending on sensitivity required, ease of conjugation with the compound, stability requirements, available instrumentation, and disposal provisions. In general, a detector which monitors a probe-target nucleic acid hybridization is adapted to the particular label which is used. Typical detectors include spectrophotometers, phototubes and photodiodes, microscopes, scintillation counters, cameras, film and the like, as well as combinations thereof. Examples of suitable detectors are widely available from a variety of commercial sources known to persons of skill. Commonly, an optical image of a substrate comprising a nucleic acid array with particular set of probes bound to the array is digitized for subsequent computer analysis.

Because incorporation of radiolabeled nucleotides into nucleic acids is straightforward, this detection represents a preferred labeling strategy. Exemplar technologies for incorporating radiolabels include end-labeling with a kinase or phosphatase enzyme, nick translation, incorporation of radio-active nucleotides with a polymerase and many other well known strategies.

Fluorescent labels are also preferred labels, having the advantage of requiring fewer precautions in handling, and being amendable to high-throughput visualization techniques. Preferred labels are typically characterized by one or more of the following: high sensitivity, high stability, low background, low environmental sensitivity and high specificity in labeling. Fluorescent moieties, which are incorporated into the labels of the invention, are generally are known, including Texas red, dixogenin, biotin, 1- and 2-aminonaphthalene, p,p'-diaminostilbenes, pyrenes, quaternary phenanthridine salts, 9-aminoacridines, p,p'-diaminobenzophenone imines, anthracenes, oxacarbocyanine, merocyanine, 3-aminoequilenin, perylene, bis-benzoxazole, bis-p-oxazolyl benzene, 1,2-benzophenazin, retinol, bis-3-aminopyridinium salts, hellebrigenin, tetracycline, sterophenol, benzimidazolylphenylamine, 2-oxo-3-chromen, indole, xanthen, 7-hydroxycoumarin, phenoxazine, calicylate, strophanthidin, porphyrins, triarylmethanes and flavin. Individual fluorescent compounds which have functionalities for linking to an element desirably detected in an apparatus or assay of the invention, or which can be modified to incorporate such functionalities include, e.g., dansyl chloride; fluoresceins such as 3,6-dihydroxy-9-phenylxanthydrol; rhodamineisotiliocyanate; N-phenyl 1-amino-8-sulfonatonaphthalene; N-phenyl 2-amino-6-sulfonatonaphthalene; 4-acetamido-4-isothiocyanato-stilbene-2,2'-disulfonic acid; pyrene-3-sulfonic acid; 2-toluidinonaphthalene-6-sulfonate; N-phenyl-N-methyl-2-aminoaphthalene-6-sulfonate; ethidium bromide; stebrine; auromine-0,2-(9'-anthroyl) palmitate; dansyl phosphatidylethanolamine; N,N'-dioctadecyl oxacarbocyanine: N,N'-dihexyl oxacarbocyanine; merocyanine, 4-(3'-pyrenyl)stearate; d-3-aminodesoxy-equilenin; 12-(9'-anthroyl)stearate; 2-methylanthracene; 9-vinylanthracene; 2,2'(vinylene-p-phenylene)bisbenzoxazole; p-bis (2-(4-methyl-5-phenyl-oxazolyl))benzene; 6-dimethylamino-1,2-benzophenazin; retinol; bis(3'-aminopyridinium) 1,10-decanediyl diiodide; sulfonaphthylhydrazone of hellibrienin; chlorotetracycline; N-(7-dimethylamino-4-methyl-2-oxo-3-chromenyl)maleimide; N-(p-(2-benzimidazolyl)-phenyl)maleimide; N-(4-fluoranthyl)maleimide; bis (homovanillic acid); resazarin; 4-chloro-7-nitro-2,1,3-benzooxadiazole; merocyanine 540; resorufin; rose bengal; and 2,4-diphenyl-3(2H)-furanone. Many fluorescent tags are commercially available from SIGMA chemical company (Saint Louis, Mo.), Molecular Probes, R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), and Applied Biosystems (Foster City, Calif.) as well as other commercial sources known to one of skill.

5.6. Apparatus for Use in Method of Determination of the Molecular Barcode of a Biological Sample The methods of the present invention are advantageously applied to control microfluidic processors to perform predetermined analyses of biological and medical samples. Exemplary analyses include determining the presence of certain nucleic acids or proteins that may indicate a disease state of an organism and help in diagnosing the disease state.

Figure 3:
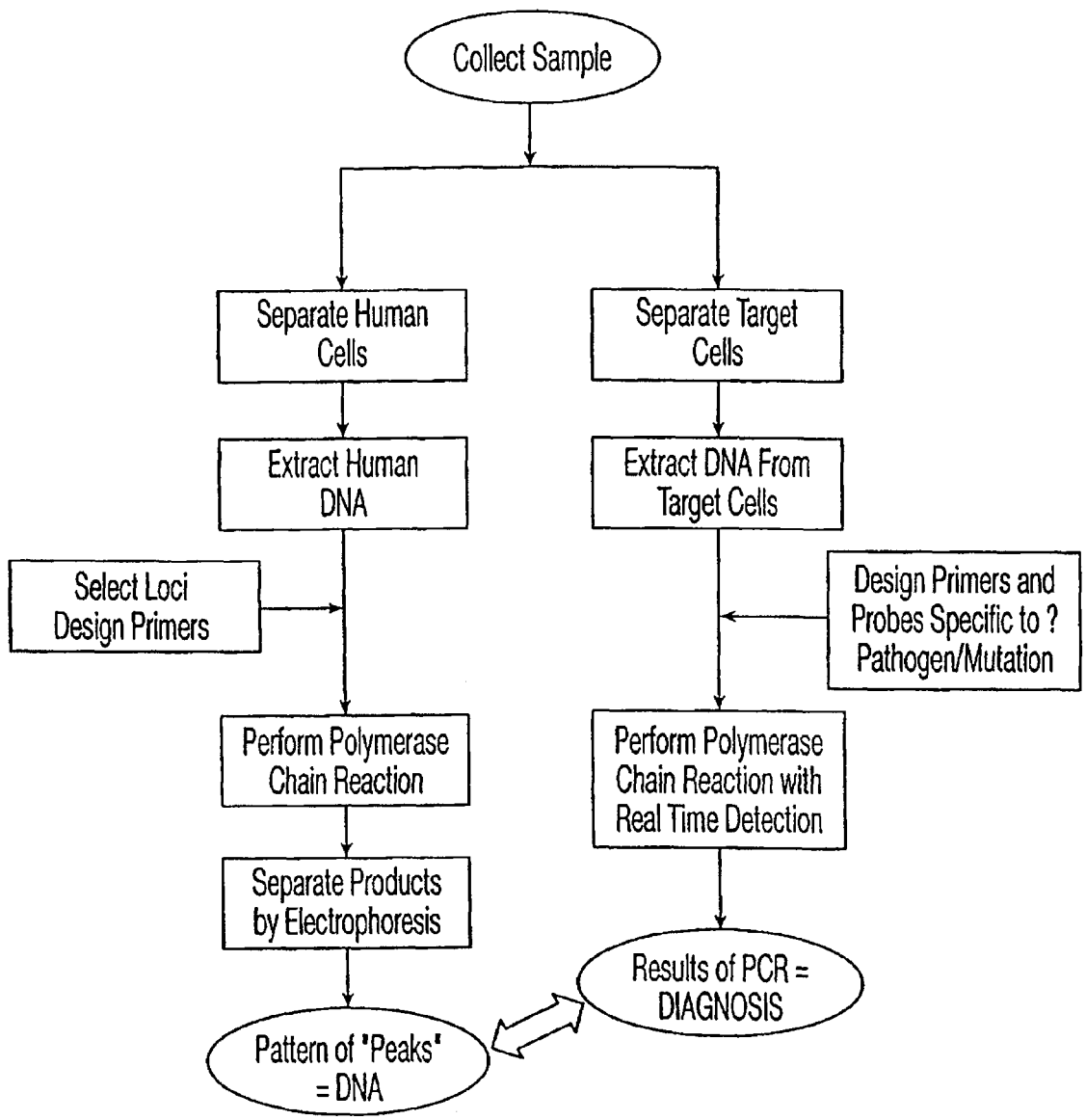
FIG. 3 depicts an illustration of the preparation and analysis of biological samples.

Accordingly, FIG. 3 illustrates the preparation and analysis of such samples. First, a biological or medical specimen is obtained, such as samples obtained from the exterior of an organism, for example, by scraping or swabbing, or from the interior of an organism, for example, by biopsy or surgical specimen. Next a sample is prepared from the specimen. This may include the steps of purifying the specimen from extraneous material (removing cells where extracellular material is to be analyzed), lysing cell (where intracellular materials are to be analyzed), separating the type of material to be analyzed from other tapes (for example, nucleic acids from proteins). Finally, the prepared sample is loaded into a microfluidic processor for analysis by the systems and methods of this invention.

The present invention provides control methods, control systems, and control software for microfluidic devices that operate by moving discrete micro-droplets through a sequence of determined configurations. Such microfluidic devices are preferably constructed in a hierarchical and modular fashion which is reflected in the preferred structure of the provided methods and systems. In particular, the methods are structured into low-level device component control functions, middle-level actuator control functions, and high-level micro-droplet control functions. Advantageously, a microfluidic device may thereby be instructed to perform an intended reaction or analysis by invoking micro-droplet control function that perform intuitive tasks like measuring, mixing, heating, and so forth. The systems are preferably programmable and capable of accommodating microfluidic devices controlled by low voltages and constructed in standardized configurations. Advantageously, a single control system can thereby control numerous different reactions in numerous different microfluidic devices simply by loading different easily understood micro-droplet programs. Suitable microfluidic systems are described in copending application Ser. No. 09/819,105, filed Mar. 28, 2001, Ser. No. 09/953,921, filed Sep. 18, 2001, and Ser. No. 10/014,519, filed Dec. 14, 2001, each of which applications is incorporated herein by reference.

In accordance with one aspect of the present invention, the microfluidic processor device apparatus may be used in accordance with the method of the present invention for identification of a biological sample of a mammal, which comprises the steps of:

a) obtaining a genomic DNA sample from said mammal;

b) performing amplification of the genomic DNA sample using at least two primers for amplification of at least two DNA markers; and c) identifying the amplified DNA markers from step b), wherein the genomic DNA sample's unique combination of amplified markers represents the molecular barcode for identification of the biological sample.

In accordance with a preferred aspect of the present invention, the microfluidic processor device apparatus may be used in accordance with the method of the present invention for identification of a biological sample of a mammal, which comprises the steps a) obtaining a genomic DNA sample from said mammal;

b) performing DNA amplification of the genomic DNA sample using at least two primers for amplification of at least two DNA markers, wherein said primers are selected from the group consisting of SEQ ID NOS:1 to 10 and complementary sequences thereto; and c) identifying the amplified DNA markers from step b), wherein the genomic DNA sample's unique combination of amplified markers represents the molecular barcode for identification of the biological sample.

In accordance with yet another aspect of the present invention, the microfluidic processor device apparatus may be used in accordance with the method of the present invention for identification of a biological sample of a subject undergoing diagnosis to determine whether the subject is afflicted with a particular disease or disorder, or is at risk of developing a particular disorder comprising a) obtaining a genomic DNA sample from a subject;

b) performing DNA amplification of the genomic DNA sample using at least two primers for amplification of at least two DNA markers;

c) identifying the amplified DNA markers of step b), wherein the genomic DNA sample's unique combination of amplified markers represents the molecular barcode for identification of the biological sample; and d) performing diagnosis of the subject's genomic DNA sample to determine whether the subject is afflicted with a particular disease or disorder, or is at risk of developing a particular disease or disorder, wherein the result obtained from said diagnosis step is thereby intimately associated with the molecular barcode of the sample of the subject being diagnosed.

In accordance with yet another aspect of the present invention, the microfluidic processor device apparatus may be used in accordance with the method of the present invention for identification of a biological sample of a subject undergoing screening for genetic lesions or mutations to determine if the subject with a lesioned gene is at risk for a disease or disorder characterized by aberrant expression or activity of a given polypeptide comprising a) obtaining a genomic DNA sample from a subject;

b) performing DNA amplification of the genomic DNA sample using at least two primers for amplification of at least two DNA markers;

c) identifying the amplified DNA markers of step b), wherein the genomic DNA sample's unique combination of amplified markers represents the molecular barcode for identification of the biological sample;

d) performing screening of the subject's genomic DNA sample for detection of genetic lesions or mutations in said genomic DNA sample to determine if a subject with a lesioned gene is at risk for a disease or disorder characterized by aberrant expression or activity of a given polypeptide; wherein the result obtained from said screening step is thereby intimately associated with the molecular barcode of the sample of the subject being screened.

In accordance with yet another aspect of the present invention, the microfluidic processor device apparatus may be used in accordance with the method of the present invention for identification of a biological sample of a subject being diagnosed for the presence of a target microorganism comprising a) obtaining a genomic DNA sample from a subject;

b) performing DNA amplification of the genomic DNA sample using at least two primers for amplification of at least two DNA markers; and c) identifying the amplified DNA markers of step b), wherein the genomic DNA sample's unique combination of amplified markers represents the molecular barcode for identification of the biological sample; and d) performing diagnosis of said subject to detect the presence of a target microorganism; wherein the result obtained from said diagnosis step is thereby intimately associated with the molecular barcode of the sample of the subject being diagnosed.

In accordance with yet another aspect of the present invention, the microfluidic processor device apparatus may be used in accordance with the method of the present invention for identification of a biological sample of a subject undergoing paternity screening, genetic screening, prenatal diagnosis, presymptomatic diagnosis, disease carrier detection, or forensic chemical analysis comprising a) obtaining a genomic DNA sample from a subject;

b) performing DNA amplification of the genomic DNA sample using at least two primers for amplification of at least two DNA markers;

c) identifying the amplified DNA markers of step b), wherein the genomic DNA sample's unique combination of amplified markers represents the molecular barcode for identification of the biological sample; and d) performing paternity screening, genetic screening, prenatal diagnosis, presymptomatic diagnosis, disease carrier detection, forensic chemical analysis, or any combination thereof, of the subject's genomic DNA sample, wherein the result obtained from said paternity screening, genetic screening, prenatal diagnosis, presymptomatic diagnosis, disease carrier detection, or forensic chemical analysis step is thereby intimately associated with the molecular barcode of the sample of the subject being screened or diagnosed.

5.7. Kits for Use in the Methods of the Invention

The methods of the present invention can be facilitated by the use of kits which contain the reagents required for carrying out the genotyping, diagnostic and/or prognostic methods of the present invention. The kits can contain reagents for carrying out the analysis of a single polymorphic restriction site (for use in, e.g., diagnostic methods) or multiple polymorphic restriction sites (for use in, e.g., genomic mapping). When multiple samples are analyzed, multiple sets of the appropriate primers and oligonucleotides are provided in the kit. In addition to the primers and oligonucleotides required for carrying out the various methods, the kits may contain the enzymes used in the methods, and the reagents for detecting the labels, e.g., the substrates for enzyme labels, etc. The kits can also contain solid substrates for used in carrying out the method of the invention. For example, the kits can contain solid substrates, such as glass plates or silicon or glass microchips, containing arrays of nucleic acid probes.

Thus, in accordance with the present invention, the methods of the invention can be facilitated by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a particular gene encoding a polypeptide, coupled with the identification of the molecular barcode of the biological sample, wherein the result obtained from the diagnosis is associated with the unique molecular barcode of the genotype of the subject being diagnosed.

In accordance with another aspect of the present invention, a kit is provided which contains the microfluidic device apparatus of the present invention, primers for a diagnosing the presence of a particular infectious agent or disease, and instructions for use.

The present invention also encompasses kits for use in sample tracking or quality control during sample processing. In one embodiment, the kit comprises a plurality of separate containers, each container containing one or more reagents for determining the unique molecular barcode of a biological sample, and instructions for use.

In yet another embodiment, the kit comprises a plurality of separate containers, each container containing one or more amplification primer reagents for determining the unique molecular barcode of a biological sample, and wherein said amplification primers are selected from the group consisting of the following primer pairs:

```
D3S1358
5' Primer
ACTGCAGTCCAATCTGGGT          (SEQ ID NO: 1)

3' primer
ATGAAATCAACAGAGGCTTG;        (SEQ ID NO: 2)

D5S818
5' Primer
GGGTGATTTTCCTCTTTGGT         (SEQ ID NO: 3)
```

-continued
```
3' primer
TGATTCCAATCATAGCCACA;        (SEQ ID NO: 4)

D7S820
5' Primer
TGTCATAGTTTAGAACGAACTAACG    (SEQ ID NO: 5)

3' primer
CTGAGGTATGAAAAACTCAGAGG;     (SEQ ID NO: 6)

D13S317
5' Primer
ACAGAAGTCTGGGATGTGGA         (SEQ ID NO: 7)

3' primer
GCCCAAAAAGACAGACAGAA;        (SEQ ID NO: 8)
and

D16S539
5' Primer
GATCCCAAGCTCTTCCTCTT         (SEQ ID NO: 9)

3' primer
ACGTTTGTGTGTGCATCTGT,        (SEQ ID NO: 10)
and
```
instructions for use.

6. EXAMPLES

6.1. STR Analysis

As noted above, there are three types of DNA variability that are commonly used in DNA fingerprinting: restriction fragment length polymorphism (RFLPs), variable number of tandem repeats (VNTRs), and short tandem repeats (STRs). STR analysis is a popular method of DNA fingerprinting, and is one of the techniques employed for use in conjunction with the HandyLab microfluidic device apparatus of the present invention.

STRs, also known as microsatellite repeats, consist of repeated sequences of two to seven bases. For example, the $[GT]_4$ repeat is GTGTGTGT and $[GAG]_6$ is CAGCCAGCAGCAGCAG. The human genome contains hundreds of thousands of these STRs evenly distributed on all chromosomes. Consequently, there are thousands of each kind of repeat; that is, thousands of [GT]~, [CAG]~, [CTG]~, [GATA]~, etc. As a result, unequivocal determination of the molecular barcode of a sample depends upon the unique DNA flanking sequences on each side of a repeat. These flanking sequences allow the analyst to zero in on a defined area of a hundred or so bases in a human genome that contains three billion bases.

Figure 1:
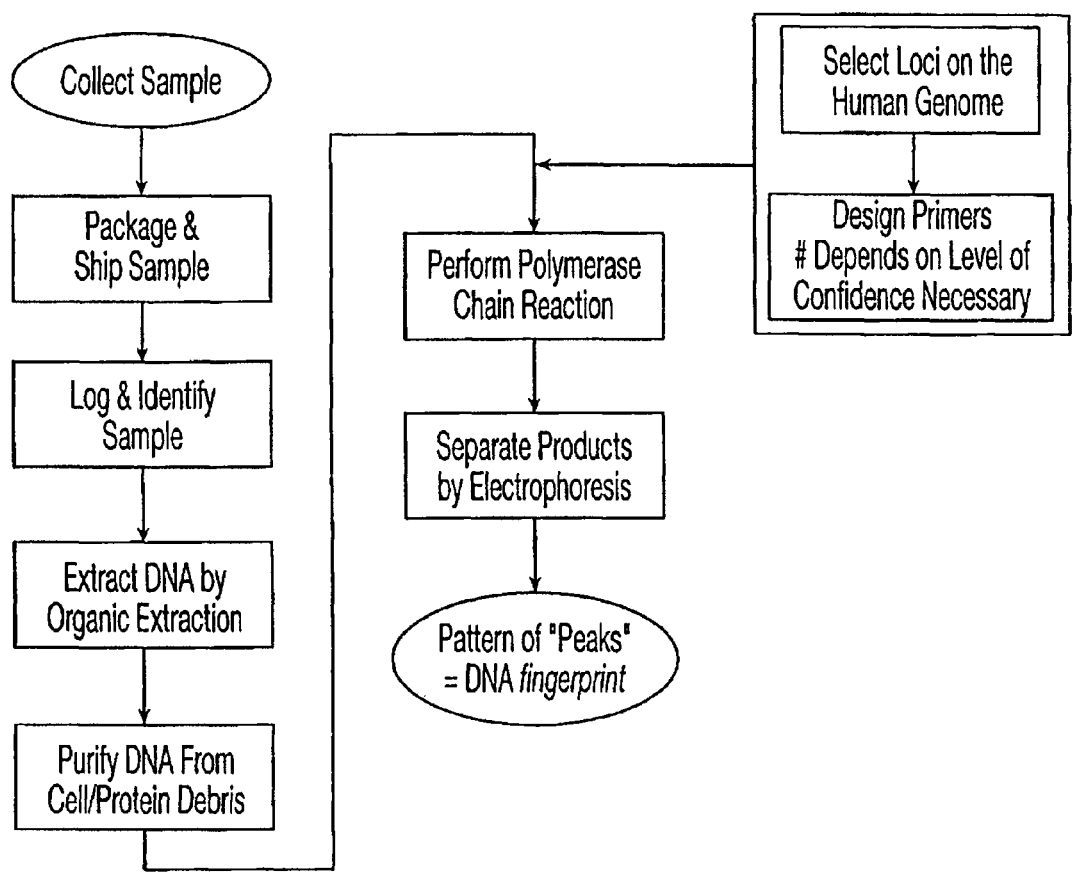
FIG. 1 depicts a flow diagram depicting the steps involved in a typical DNA fingerprint analysis.

By way of illustration, the STR designated D7S820 (GenBank number G086 16), located on human chromosome 7, contains a [GATA]~ repeat, where n can range from 6 to 14. The DNA sequence of a D7S820 STR with twelve GATA repeats is reproduced below with the $[GATA]_{12}$ region capitalized and the unique flanking regions underlined: aattttgta ttttttttag agacggggtt tcaccatgtt ggtcaggctg actatggagt tattttaagg ttaatatata taaagggtat gatagaacac ttgtcata~tttagaacgaactaacGATAG ATAGATAGAT AGATAGATAG ATAGATAGAT AGATAGATAG ATAgacagat tgatagtttt ttttttatctc actaaatagt ctatagtaaa catttaatta ccaatatttg gtgcaattct gtcaatgagg ataaatgtgg aatcgttata attcttaaga atatattc cctct~aattttatacct ~gattttaa ggcc It is these flanking sequences that are used to amplify the region between them. The amplification procedure, known as the polymerase chain reaction (PCR), enzymatically synthesizes thousands of copies of the intervening DNA region. This amplification enables forensic laboratories to generate enough DNA for analysis from hair roots and blood samples. Only one nanogram of DNA is required for a successful PCR. In a separate reaction, the PCR products have their DNA sequence determined. This sequence reveals the number of repetitive units in the sample. A flow diagram depicting the steps involved in a typical DNA fingerprint analysis as conducted in most forensic laboratories is depicted in FIG. 1.

Figure 2:
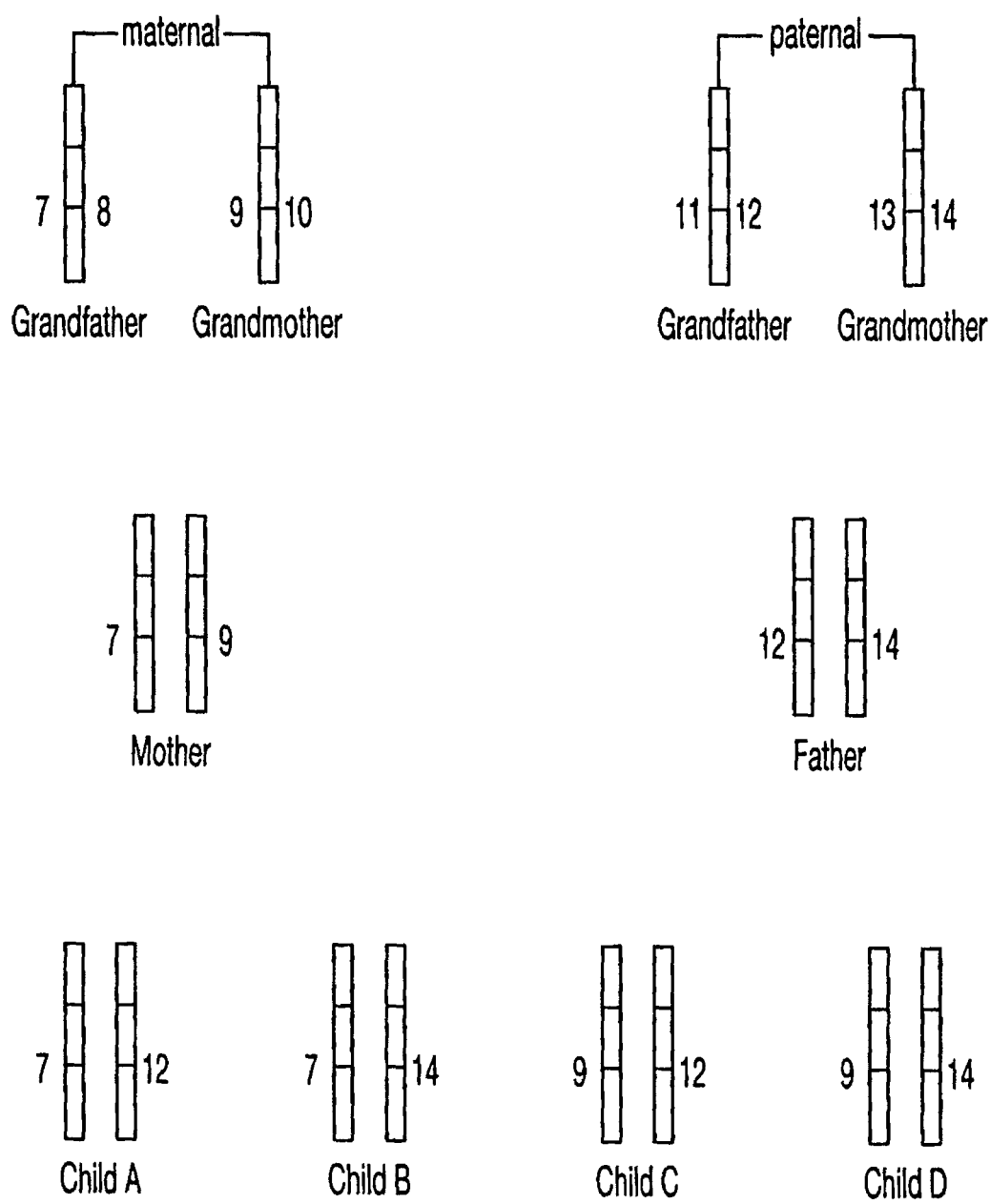
FIG. 2 depicts a chromosome diagram depicting STR variability in D7S820 from grandparents to parents to grandchildren.

A person inherits an equal amount of nuclear DNA from each parent. Therefore, among all the other DNA passed down from one's father and mother, one inherits one maternal copy of D7S 820, and one paternal copy of D7S820. The chromosome diagram depicted in FIG. 2 tracks STR variability in D7S820 from grandparents to parents to grandchildren. For ease in following the example, each copy of D7S820 has a different number of [GATA] repeat units. For example, the maternal grandfather has one chromosome 7 with [GATA]$_7$ in its D7S820 STR, and another chromosome 7 with [GATAJ$_8$ in its D7S 820 STR. His daughter inherited his [GATAb STR and his wife's [GATA]$_9$ STR. The relationship of child to parent can therefore be followed using this one marker.

6.2. Determination of the Molecular Barcode of a Biological Sample Using Short Tandem Repeat Sequences Short Tandem Repeat (STR) loci consist of 3-7 nucleotide repetitive elements. They are highly polymorphic in both length and the sequences of the repeats, which makes them important genetic markers for mapping studies, disease diagnosis and human identity testing. The Polymerase Chain Reaction (PCR) makes it possible to analyze very small amounts of DNA much faster. In fingerprinting work mostly STRs with four or five base pair repeats are used. The detection of the polymorphisms of STR loci is based primarily on the analysis of the length by means of electrophoresis in polyacrylamide gels.

Materials and Methods:

The buccal epithelial cells of four healthy volunteers were collected with buccal swabs. The genomic DNA was extracted from them using standard procedures (Puregene, Gentra Systems). The DNA was amplified using five specific STR markers from the Combined DNA Index System (CODIS). The five different STR markers used were D3S1358, D5S818, D7S820, D13S317, and D16S539. The primer sequences of these markers were obtained from the GenBank public database as shown in Table 1. The primers were synthesized by Invitrogen Technologies. The real time PCR was carried out in a Light Cycler (Roche Molecular Biochemicals). Each PCR reaction contained 20 ng of genomic DNA, 1.51 μl of 10××SYBR PCR reaction mix (Roche Molecular Biochemicals), 0.9 μl of 25 mM Magnesium chloride (final concentration of 1.5 mM), 0.125 μl of 60 μM forward and reverse primer each (final concentration of 7.5 μM) in a final volume of 15 μl reaction. Conditions used for the PCR was 94° C. for 2 mm, then 50 cycles of 94° C. for 5 sec, 60° C. for 5 sec, 72° C. for 10 sec. After the PCR was carried out, 5 μl of 2× loading buffer (Invitrogen Technologies) was added. The reactions were denatured at 95° C. for 2 mm and immediately placed them on ice. Then 3 μl of the samples were loaded on a 10% denaturing TBE-Urea polyacrylamide gel (BioRad). Along with the samples, loaded 6 μl of 25 bp ladder (Invitrogen Technologies) and Ffv allelic ladder mix (Promega). As used herein, the first F refers to F13A01, the second F refers FESFPS, and the v refers to WA. The size of the FFv allelic ladder ranges from 120 bp to 330 bp. Electrophoresis was carried out at 200V for 2 hours with 1×TBE buffer. The gels were post stained with 1×SYBR green dye (BMA) for 10 min and the gels photographed. The above procedure was repeated twice with additional DNA standards such as 10 bp, 8 bp and 20 bp DNA standards. Simultaneously, the same genomic DNA used in amplifying the above markers was used to detect mutations in Factor V Leiden Kit and Apo B Mutation detection Kit (Roche Molecular Biochemicals) as a model system for the methods of the present invention. The respective reactions were carried out and the results were interpreted according to the manufacturer's protocol.

TABLE 1

The STR markers with the forward and reverse primer sequences that were used for determination of the molecular barcode of the sample.[1]

| STR Marker | Forward Primer sequence | Reverse Primer sequence |
|---|---|---|
| D3S1358 | ACTGCAGTCCAATCTGGGT | ATGAAATCAACAGAGGCTTG |
| D5S818 | GGGTGATTTTCCTCTTTGGT | TGATTCCAATCATAGCCACA |
| D7S820 | TGTCATAGTTTAGAACGAACTAACG | CTGAGGTATCAAAAACTCAGAGG |
| D13S317 | ACAGAAGTCTGGGATGTGGA | GCCCAAAAAGACAGACAGAA |
| D16S539 | GATCCCAAGCTCTTCCTCTT | ACGTTTGTGTGTGCATCTGT |

[1]Appendix A provides the STR fact sheets (http://www.cstl.nist.gov/biotech/strbase/str_d3shtm) for each of the STR markers used in the method of the present invention. Each STR marker fact sheet provides the chromosomal location, the GenBank Accession Number, the reported primers and the PCR product sizes of the observed alleles.

Results:

FIG. 4 depicts the FYBR green dye stained polyacrylamide gel of the amplified DNAs of the respective STR markers. The letters A, B, C and D represent the particular genomic DNA samples. 25 bp ladder and Ffv, the allelic ladder were used as the reference standards to determine the sizes of the alleles.

The polyacrylamide gels were read based on the size of the FFv allelic ladder sized by the 25 bp ladder. The sizes of the alleles correspond to the number of repeat sequences in each of the allele. Since the STRs employed are tetranucleotide markers, the alleles vary by 4 base pairs each. The size of the alleles and the number of repeats was referred from the STRBase (http://www.cstl.nist.gov/biotech/strbase) for all the CODIS markers. The allele sizes and the corresponding number of repeat units interpreted from the gels are as shown in Table 2. The results of the repeated gels were identical, thus confirming the reproducibility of the reading of the gel (data not shown). The genotype frequency of each individual's combined profile for all the five markers typed can be calculated using http://www.csfs.ca/pplus/profiler.htm. The calculations are shown in Appendix A

TABLE 2

Allele sizes and the corresponding number of repeat units as interpreted from the gels.

| STR Marker | A Allele Sizes | Sizes | B Allele Sizes | Sizes | C Allele Sizes | Repeats | D Allele Sizes | Repeats |
|---|---|---|---|---|---|---|---|---|
| D3S1358 | 127/123 | 15/14 | 135/123 | 17/14 | 135/131 | 17/16 | 127/123 | 15/14 |
| D5S818 | 161/149 | 12/9 | 149/145 | 9/8 | 153/145 | 10/8 | 157/145 | 11/8 |
| D7S820 | 206/206 | 8/8 | 206/194 | 8/5 | 201/194 | 6/5 | 202/198 | 7/6 |
| D13S317 | 185/185 | 12/12 | 185/181 | 12/11 | 193/169 | 14/8 | 193/173 | 14/9 |
| D16S539 | 157/153 | 11/10 | 141/141 | 5/5 | 153/141 | 10/5 | 161/149 | 12/9 |

The Factor V Leiden Mutation Detection Kit permits the detection of a single point mutation of the human Factor V gene. The wildtype genotype results in a higher melting temperature ($T_M$) at about 65° C. The mutant genotype produces one mismatch and results in a lower $T_M$ of 57° C. Heterozygous genotypes show both the melting peaks. FIG. 5 depicts the analysis of the genomic DNA from two buccal epithelial cell samples that were used to detect mutations with the Factor V Leiden mutation kit. A is the positive control, which is a heterozygous mutant. B and C are the two buccal epithelial cell samples. D is the negative control without the template. From this result, it is clear that the two buccal samples B and C are wildtype, without the human Factor V gene point mutation.

The Apo B mutation Detection Kit permits the detection of two point mutations at nucleotide position 9774 and 9775 of the human Apolipoprotein B gene. The wildtype genotype results in a $T_M$ of about 62.5° C. The C9774T or G9775A point mutation results in a TM of 57° C. and 53° C. respectively. The heterozygous genotypes show the melting peaks at 57° C. and 62.5° C. or 53° C. and 62.5° C. respectively. FIG. 6 depicts the Apo B mutation analysis of the genomic DNA that was used for determination of the molecular barcode of the genomic DNA of the buccal epithelial cell samples, and that was also used in detecting the point mutation in the Factor V Leiden kit. A—Heterozygous positive control with 9775 point mutation; B—heterozygous positive control with 9774 mutation; C and D are the two buccal epithelial cell samples are wildtype; E-negative control without any template. From this result, it is clear that the two C and D samples are wildtype, without the Apo B point mutation.

Thus, this experiment demonstrates the applicability of the method to identify a given mutation in the genomic DNA sample of an individual, as well as determine the unique molecular barcode of the genotype of the subject being diagnosed using the individual's unique combination of amplified markers.

6.3. Determination of the Molecular Barcode of a Biological Sample Using Short Tandem Repeat Sequences: Blind Sample Identification Experiment:

Materials and Methods:

The genomic DNA from heterozygous major (heterozygous mutant), homozygous major (wildtype genotype) and homozygous minor (homozygous mutant) individuals for the Factor V mutation was obtained from Stratagene, Inc. PCR was conducted using the primers and probe from Factor V Leiden mutation detection kit (Roche Molecular Biochemicals) and the respective mutations confirmed as described above. The DNA of these individuals was also genotyped with the five STR markers—D3S1358, D5S818, D7S820, D13S317 and D16S539. The PCR was carried out realtime in the Light cycler (Roche Molecular Biochemicals). Each PCR reaction of the five STRs contained 5 ng of genomic DNA, 1.5 µl of 10×SYBR PCR reaction mix (Roche Molecular Biochemicals), 0.9 µl of 25 mM magnesium chloride (final concentration of 1.5 mM), 0.125 µl of 60 µM forward and reverse primer each (final concentration of 7.5 µM) in a final volume of 15 pl reaction. Conditions used for the PCR were 94° C. for 2 min, then 50 cycles of 94° C. for 5 sec, 60° C. for 5 sec, 72° C. for 10 sec.

The blind sample identification experiment was conducted as follows. The three genomic DNA samples from the heterozygous major, homozygous major and homozygous minor individuals for the Factor V mutation were randomly blind masked to hide the true identity of the individuals' DNA. The masked tubes were then labeled as (a), (b) and (c). The PCR reaction for the mutation detection was carried out according to the manufacturers' protocol. Each reaction had 1.5 µl of 10× mutation detection mix containing the primers, probe, the PCR buffer, magnesium chloride, dNTPs, polymerase enzyme to which was added 5 ng of DNA from the masked tube samples. The PCR was performed using the conditions 95° C. for 30 sec, 45 cycles of 55° C. for 10 sec and 72° C. for 10 sec, a melting step of 95° C. for 0 sec, 45° C. for 60 sec and 75° C. for 10 sec.

Results:

The resultant DNA bands were separated using 10% polyacrylamide gels (BioRad) by electrophoresis at 190V for 1.5 hrs. FIG. 7 shows the FYBR green stained gels of the blind sample identification experiment conducted with the Factor V genomic DNA. Sample 1 is the heterozygous major (heterozygous mutant) individual for the Factor V mutation; sample 2 is the homozygous major (wildtype genotype) individual for the Factor V mutation; and sample 3 is the homozygous minor (homozygous mutant) individual for the Factor V mutation. Based on the size of the FYBR green stained DNA bands and their pattern of migration, sample individual (a) was identified as homozygous major, sample individual (b) was identified as homozygous minor and sample individual (c) was identified as heterozygous major. The allele sizes and the corresponding number of repeats are given in Table #3 below.

TABLE 3

Allele sizes and the corresponding number of repeat units as interpreted from the gels:

| STR Marker | Sample 1/c Allele Sizes | Repeats | Sample 2/a Allele Sizes | Sizes | Sample 3/b Allele Sizes | Repeats |
|---|---|---|---|---|---|---|
| D3S1358 | 135/127 | 17/15 | 131/123 | 16/14 | 127/127 | 15/15 |
| D5S818 | 149/145 | 9/8 | 149/145 | 9/8 | 145/145 | 8/8 |
| D7S820 | 206/198 | 8/6 | 202/198 | 7/6 | 206/202 | 8/7 |
| D13S317 | 173/169 | 9/8 | 177/173 | 10/9 | 177/173 | 10/9 |
| D16S539 | 153/145 | 10/8 | 153/149 | 10/9 | 153/140 | 10/9 |

Sample 1/c = heterozygous major.
Sample 2/a = homozygous major.
Sample 3/b = homozygous minor.

FIG. 8 depicts the analysis of the genomic DNA from the three individual samples (heterozygous major (1), homozygous major (2), and homozygous minor (3), respectively) that were used to detect mutations the Factor V genomic DNA with the Factor V Leiden mutation kit in the blind sample identification experiment. From FIG. 9, it is clear that homozygous major (wildtype genotype) Factor V mutation has a melting temperature of 65° C., the heterozygous major (heterozygous mutant) Factor V mutation has a melting temperature of 57° C. and 65° C., whereas the homozygous minor (homozygous mutant) Factor V mutation has a melting temperature of 57° C.

FIG. 9 depicts the analysis of the blind sample identification experiment in which individual samples 1-3 were also masked to hide their identities and subsequently labeled arbitrarily as individual samples a-c. From FIG. 10, it is clear that individual sample a represents the homozygous major (wildtype genotype) Factor V mutation as it has a melting temperature of 65° C., individual sample b represents the homozygous minor (homozygous mutant) Factor V mutation as it has a melting temperature of 57° C., and individual sample c represents the heterozygous major (heterozygous mutant) Factor V mutation as it has a melting temperature of 57° C. and 65° C.

Thus, the results show in FIGS. 9 and 10 confirm that individual sample a is the homozygous major Factor V individual, individual sample b is the homozygous minor Factor V individual and individual sample c is the heterozygous major Factor V individual, thereby confirming the original identity of the masked individual samples without any error. This blind sample identification experiment also demonstrates the applicability of the method to unequivocally identify the molecular barcode for identification of a biological sample using the genomic DNA sample's unique combination of amplified markers.

6.4. Working or Prophetic Example of HandyLab Apparatus with STR Analysis

In this example, the preparation and analysis of biological samples using the HandyLab apparatus and methods of the invention are illustrated. First, a biological or medical specimen is obtained, such as samples obtained from the exterior of an organism, for example, by scraping or swabbing, or from the interior of an organism, for example, by biopsy or surgical specimen. Next a sample is prepared from the specimen. This may include the steps of purifying the specimen from extraneous material (removing cells where extracellular material is to be analyzed), lysing cell (where intracellular materials are to be analyzed), separating the type of material to be analyzed from other types (for example, nucleic acids from proteins). Finally, the prepared sample is loaded into a microfluidic processor for analysis by the methods of this invention.

In particular, the microfluidic processor HandyLab apparatus may be used in accordance with the methods of the present invention to unequivocally identify a biological sample obtained during paternity screening or genetic screening of a subject using the following steps: a) obtaining a biological sample from a subject; b) performing paternity screening or genetic screening on said biological sample; and c) simultaneously identifying the DNA fingerprint of the biological sample, wherein the result obtained from said screening is associated with the unique DNA fingerprint biological barcode of the genotype of the subject being screened.

The microfluidic processor HandyLab apparatus may also be used to unequivocally identify a biological sample obtained during prenatal diagnosis or presymptomatic diagnosis of a subject using the following steps: a) obtaining a biological sample from a subject; b) performing prenatal diagnosis or presymptomatic diagnosis on said biological sample; and c) simultaneously identifying the DNA fingerprint of the biological sample, wherein the result obtained from the diagnosis is associated with the unique DNA fingerprint biological barcode of the genotype of the subject being diagnosed.

The microfluidic processor HandyLab apparatus may additionally be used to unequivocally identify a biological sample obtained during carrier detection analysis or forensic chemical analysis of a subject using the following steps: a) obtaining a biological sample from a subject; b) performing carrier detection analysis or forensic chemical analysis on said biological sample; and c) simultaneously identifying the DNA fingerprint of the biological sample, wherein the result obtained from said analysis is associated with the unique DNA fingerprint biological barcode of the genotype of the subject being analyzed.

The microfluidic processor HandyLab apparatus may also be used to unequivocally identify a biological sample obtained during the diagnosis of a subject to determine whether a subject is afflicted with a particular disease or disorder, or is at risk of developing a particular disorder using the following steps: a) obtaining a biological sample from a subject; b) diagnosing a subject to determine whether a subject is afflicted with a particular disease or disorder, or is at risk of developing a particular disorder; and c) simultaneously identifying the DNA fingerprint of the biological sample, wherein the result obtained from the diagnosis is associated with the unique DNA fingerprint biological barcode of the genotype of the subject being diagnosed.

The microfluidic processor HandyLab apparatus may also be used to unequivocally identify a biological sample obtained during the diagnosis of a subject to detect the presence of a target microorganism using the following steps: a) obtaining a biological sample from a subject; b) diagnosing a subject to detect the presence of a target microorganism in said biological sample; and c) simultaneously identifying the DNA fingerprint of the biological sample, wherein the result obtained from the diagnosis is associated with the unique DNA fingerprint biological barcode of the genotype of the subject being diagnosed.

All references cited herein are incorporated herein by reference in their entirety and for all purposes to the same extent as if each individual publication or patent or patent application was specifically and individually indicated to be incorporated by reference in its entirety for all purposes.

Many modifications and variations of the present invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

APPENDIX A

| Other Names | Chromosomal Location | GenBank Accession |
|---|---|---|
|  | 3p | 11449919; has 12 repeats |

Repeat: [AGAT], [TCTA]=bottom strand

| Reported Primers | Ref. | PCR Primer Sequences |
|---|---|---|
| Set 1 | 148, | 5'-ACT GCA GTC CAA TCT GGG T-3' (AGAT strand) |
|  | 502 | 5'-ATG AAA TCA ACA GAG GCT TG-3' (TCTA strand) |
| Set 2 | ABI | AmpFlSTR ®® Profiler Plus ™™ |
| Set 3 | Promega | GenePrint ®® PowerPlex ™™ 2.1 |

PCR Product Sizes of Observed Alleles

| Allele (Repeat #) | Set 1, 3 | Set 2 | Repeat Structure | Ref. |
|---|---|---|---|---|
| 8 | 99 bp | 97 bp |  | variant allele |
| 9 | 103 bp | 101 bp |  | SGM Plus |
| 10 | 107 bp | 105 bp |  | SGM Plus |
| 11 | 111 bp | 109 bp |  | SGM Plus |
| 12 | 115 bp | 113 bp |  | SGM Plus |
| 13 | 119 bp | 117 bp | TCTA[TCTG]$_2$[TCTA]$_{10}$ | 729 |
| 14 | 123 bp | 121 bp | TCTA[TCTG]$_2$[TCTA]$_{11}$ | 668 |
| 15 | 127 bp | 125 bp | TCTA[TCTG]$_3$[TCTA]$_{11}$ | 668 |
| 15' | 127 bp | 125 bp | TCTA[TCTG]$_2$[TCTA]$_{12}$ |  |
| 15.2 | 129 bp | 127 bp |  | SGM Plus |
| 16 | 131 bp | 129 bp | TCTA[TCTG]$_3$[TCTA]$_{12}$ | 668 |
| 16' | 131 bp | 129 bp | TCTA[TCTG]$_2$[TCTA]$_{13}$ | 729 |
| 16.2 | 133 bp | 131 bp |  | 642 |
| 17 | 135 bp | 133 bp | TCTA[TCTG]$_3$[TCTA]$_{13}$ | 668 |
| 17' | 135 bp | 133 bp | TCTA[TCTG]$_2$[TCTA]$_{14}$ | 729 |
| 17.1 | 136 bp | 134 bp |  | SGM Plus |
| 18 | 139 bp | 137 bp | TCTA[TCTG]$_3$[TCTA]$_{14}$ | 668 |
| 18.3 | 142 bp | 140 bp |  | variant allele |
| 19 | 143 bp | 141 bp | TCTA[TCTG]$_3$[TCTA]$_{15}$ | 729 |
| 20 | 147 bp | 145 bp |  | 729 |

Allelic Ladders: Commercially available from Applied Biosystems (ladder allele range: 12-19)

Common Multiplexes AmpFlSTR Blue, PwerPlex 1.1, Profiler, Profiler Plus, and COfiler

| Other Names | Chromosomal Location | GenBank Accession |
|---|---|---|
| D5 | 5q21-q31 | G08446; has 11 repeat units |
|  |  | AC008512; has 9 repeat units |

Repeat: [AGAT]=GenBank top strand

| Reported Primers | Ref. | PCR Primer Sequences |
|---|---|---|
| Set 1 | Promega | GenePrint ®® PowerPlex ™™ 2.1 |
| Set 2 | 453 | 5'-GGGTGATTTTCCTCTTTGGT-3' |
|  |  | 5'-TGATTCCAATCATAGCCACA-3' |
| Set 3 | ABI | AmpFlSTR ®® Profiler Plus ™™ |

PCR Product Sizes of Observed Alleles

| Allele (Repeat #) | Set 1 | Set 2 | Set 3 | Repeat Structure | Ref. |
|---|---|---|---|---|---|
| 7 | 119 bp | 141 bp | 134 bp | [AGAT]$_7$ | 721 |
| 8 | 123 bp | 145 bp | 138 bp | [AGAT]$_8$ | 721 |
| 9 | 127 bp | 149 bp | 142 bp | [AGAT]$_9$ | 721 |
| 10 | 131 bp | 153 bp | 146 bp | [AGAT]$_{10}$ | 721 |
| 11 | 135 bp | 157 bp | 150 bp | [AGAT]$_{11}$ | 721 |
| 12 | 139 bp | 161 bp | 154 bp | [AGAT]$_{12}$ | 721 |
| 13 | 143 bp | 165 bp | 158 bp | [AGAT]$_{13}$ | 721 |
| 14 | 147 bp | 169 bp | 162 bp | [AGAT]$_{14}$ | 721 |
| 15 | 151 bp | 173 bp | 166 bp | [AGAT]$_{15}$ | 721 |
| 16 | 155 bp | 171 bp | 170 bp |  | Profiler Plus |

D7S820

| Other Names | Chromosomal Location | GenBank Accession |
|---|---|---|
| D7 | 7q | G08616; has 12 repeat units |
|  |  | AC004848; has 13 repeat units |

Repeat: [GATA]=GenBank top strand

| Reported Primers | Ref. | PCR Primer Sequences |
|---|---|---|
| Set 1 | Promega | GenePrint ®® PowerPlex ™™ 1.1 |
| Set 2 | ABI | AmpFlSTR ®® Profiler Plus ™™ |
| Set 3 | 453 | 5'-TGTCATAGTTTAGAACGAACTAACG-3' |
|  |  | 5'-CTGAGGTATCAAAAACTCAGAGG-3' |

PCR Product Sizes of Observed Alleles

| Allele (Repeat #) | Set 1 | Set 2 | Set 3 | Repeat Structure | Ref. |
|---|---|---|---|---|---|
| 5 | 211 bp | 253 bp | 194 bp |  | variant allele |
| 6 | 215 bp | 257 bp | 198 bp | [GATA]$_6$ | 721 |
| 6.3 | 218 bp | 260 bp | 201 bp |  | Profiler Plus |
| 7 | 219 bp | 261 bp | 202 bp | [GATA]$_7$ | 721 |
| 7.3 | 222 bp | 264 bp | 205 bp |  | variant allele |
| 8 | 223 bp | 265 bp | 206 bp | [GATA]$_8$ | 721 |
| 8.1 | 224 bp | 266 bp | 207 bp |  | variant allele |
| 8.2 | 225 bp | 267 bp | 208 bp |  | variant allele |
| 9 | 227 bp | 269 bp | 210 bp | [GATA]$_9$ | 721 |
| 9.1 | 228 bp | 270 bp | 211 bp |  | variant allele |
| 9.3 | 230 bp | 272 bp | 213 bp |  | variant allele |
| 10 | 231 bp | 273 bp | 214 bp | [GATA]$_{10}$ | 721 |
| 10.1 | 232 bp | 274 bp | 215 bp |  | variant allele |
| 10.3 | 234 bp | 276 bp | 217 bp |  | variant allele |
| 11 | 235 bp | 277 bp | 218 bp | [GATA]$_{11}$ | 721 |
| 11.1 | 236 bp | 278 bp | 219 bp |  | variant allele |
| 12 | 239 bp | 281 bp | 222 bp | [GATA]$_{12}$ | 721 |
| 12.1 | 240 bp | 282 bp | 223 bp |  | variant allele |
| 13 | 243 bp | 285 bp | 226 bp | [GATA]$_{13}$ | 721 |

| Allele (Repeat #) | Set 1 | Set 2 | Set 3 | Repeat Structure | Ref. |
|---|---|---|---|---|---|
| 13.1 | 244 bp | 286 bp | 227 bp | | variant allele |
| 14 | 247 bp | 289 bp | 230 bp | [GATA]$_{14}$ | 721 |
| 15 | 251 bp | 293 bp | 234 bp | | Profiler Plus |

Allelic Ladders: Commercially available from Promega and Applied Biosystems
Common Multiplexes: PowerPlex, Profiler, COfiler
D13S317

| Other Names | Chromosomal Location | GenBank Accession |
|---|---|---|
| D13 | 13q22-q31 | G09017; has 13 repeat units AL353628.2 |

Repeat: [GATA]=bottom strand (commonly used); [TATC]=GenBank top strand

| Reported Primers | Ref. | PCR Primer Sequences |
|---|---|---|
| Set 1 | Promega | GenePrint ®® PowerPlex ™™ 1.1 |
| Set 2 | 453 | 5'-ACAGAAGTCTGGGATGTGGA-3'<br>5'-GCCCAAAAAGACAGACAGAA-3' |
| Set 3 | ABI | AmpF1STR ®® Profiler Plus ™™ |

PCR Product Sizes of Observed Alleles

| Allele (Repeat #) | Set 1, 2 | Set 3 | Repeat Structure | Ref. |
|---|---|---|---|---|
| 5 | 157 | 193 | | Profiler Plus |
| 7 | 165 bp | 201 | [TATC]$_7$ | 721 |
| 7.1 | 166 | 202 | | variant allele |
| 8 | 169 bp | 205 | [TATC]$_8$ | 721 |
| 8.1 | 170 | 206 | | variant allele |
| 9 | 173 bp | 209 | [TATC]$_9$ | 721 |
| 10 | 177 bp | 213 | [TATC]$_{10}$ | 721 |
| 10' | 177 | 213 | [TATC]$_{10}$ AATC | 721 |
| 11 | 181 bp | 217 | [TATC]$_{11}$ | 721 |
| 12 | 185 bp | 221 | [TATC]$_{12}$ | 721 |
| 13 | 189 bp | 225 | [TATC]$_{13}$ | 721 |
| 14 | 193 bp | 229 | [TATC]$_{14}$ | 721 |
| 15 | 197 bp | 233 | [TATC]$_{15}$ | 721 |
| 16 | 201 | 237 | | variant allele |

Allelic Ladders: Commercially available from Promega and Applied Biosystems
Common Multiplexes: PowerPlex, Profiler, Profiler Plus
D16S539

| Other Names | Chromosomal Location | GenBank Accession |
|---|---|---|
| D16 | 16q22-24 | G07925; has 11 repeat units AC024591.3 |

Repeat: [GATA]=GenBank top strand

| Reported Primers | Ref. | PCR Primer Sequences |
|---|---|---|
| Set 1 | Promega | GenePrint ®® PowerPlex ™™ 1.1 |
| Set 2 | CHLC Web Site | 5'-GATCCCAAGCTCTTCCTCTT-3'<br>5'-ACGTTTGTGTGTGCATCTGT-3' |
| Set 3 | ABI | AmpF1STR ®® Profiler Plus ™™ |

PCR Product Sizes of Observed Alleles

| Allele (Repeat #) | Set 1 | Set 2 | Set 3 | Repeat Structure | Ref. |
|---|---|---|---|---|---|
| 5 | 264 bp | 141 bp | 233 bp | [GATA]$_5$ | 721 |
| 8 | 276 bp | 145 bp | 245 bp | [GATA]$_8$ | 721 |
| 9 | 280 bp | 149 bp | 249 bp | [GATA]$_9$ | 721 |
| 10 | 284 bp | 153 bp | 253 bp | [GATA]$_{10}$ | 721 |
| 11 | 288 bp | 157 bp | 257 bp | [GATA]$_{11}$ | 721 |
| 12 | 292 bp | 161 bp | 261 bp | [GATA]$_{12}$ | 721 |
| 13 | 296 bp | 165 bp | 265 bp | [GATA]$_{13}$ | 721 |
| 13.3 | 299 bp | 168 bp | 268 bp | | variant allele |
| 14 | 300 bp | 169 bp | 269 bp | [GATA]$_{14}$ | 721 |
| 15 | 304 bp | 173 bp | 273 bp | [GATA]$_{15}$ | 721 |

Allelic Ladders: Commercially available from Promega, Applied Biosystems
Common Multiplexes: PowerPlex, COfiler

We claim:

1. A method for tracking a biological sample comprising DNA of a living mammalian subject, the method comprising:
    a) amplifying the DNA using at least two primers for amplification of at least two respective DNA markers of the DNA of the living mammalian subject, thereby creating a molecular barcode for the sample, wherein the molecular barcode comprises a unique combination of genetic markers associated with the living mammalian subject;
    b) associating the molecular barcode with the biological sample;
    c) performing a diagnostic or prognostic test on the biological sample, thereby generating test data, wherein the test data are indicative of the presence or absence of an infectious agent, a disease condition, or a disease predisposition in the living mammalian subject; and
    d) linking said test data regarding the infectious agent, a disease condition, or a disease predisposition in the living mammalian subject with the molecular barcode of the living mammalian subject, thereby tracking the sample without accidental misidentification of the test data and the living mammalian subject.

2. The method of claim 1, wherein the amplifying uses at least three primers for amplification of at least three respective DNA markers of DNA of the subject.

3. The method of claim 2, wherein the amplifying uses at least five primers for amplification of at least five respective DNA markers of DNA of the subject.

4. The method of claim 1, wherein the performing a diagnostic or prognostic test comprises:
    obtaining data indicative of the presence of a pathogen in the biological sample.

5. The method of claim 4, wherein the data indicative of the presence of the pathogen are indicative of whether the pathogen is a bacteria or a virus, and a strain thereof.

6. The method of claim 1, wherein the performing a diagnostic or prognostic test, comprises:
    detecting the presence or absence of a target microorganism in the sample.

7. The method according to claim 6, wherein the target microorganism is selected from the group consisting of virus, bacteria, fungi and protozoa.

8. The method according to claim 7, wherein the bacteria is selected from the group consisting of *Mycobacteria tuberculosis, Rickettsia rickettsii, Ehrlichia chaffeensis, Borrelia burgdorferi, Yersinia pestis, Treponema pallidum, Chlamydia trachomatis, Chlamydia pneumoniae, Mycoplasma pneumoniae, Mycoplasma* sp., *Legionella pneumophila, Legionella dumoffii, Mycoplasma fermentans, Ehrlichia* sp., *Haemophilus influenzae, Neisseria meningitidis, Streptococcus pneumonia, S. agalactiae*, and *Listeria monocytogenes*.

9. The method of claim 6, wherein the amplifying DNA to generate a molecular barcode, and the performing a diagnostic or prognostic test to detect the presence of a target microorganism are performed using a microfluidic device.

10. The method of claim 1, wherein the biological sample is divided into at least two portions, wherein DNA in a first portion is amplified, and said diagnostic or prognostic test data are obtained on a second portion.

11. The method of claim 10, wherein the sample is divided using a microfluidic device.

12. The method of claim 1, wherein the amplifying of the DNA employs a method or combination of methods selected from the group consisting of: variable number tandem repeats analysis, short tandem repeats analysis, complex tandem repeats analysis, restriction fragment length polymorphism analysis, allele specific oligonucleotide analysis, denaturation temperature analysis, single strand conformation polymorphism analysis, amplified fragment length polymorphism analysis, microsatellite or single sequence repeat analysis, rapid amplified polymorphic DNA analysis, sequence tagged site analysis, allele specific polymerase chain reaction analysis, and dynamic allele specific hybridization analysis.

13. The method of claim 1, wherein the DNA is genomic DNA.

14. The method of claim 13, wherein said diagnostic test comprises screening the subject's genomic DNA for the existence of a genetic lesion or mutation.

15. The method of claim 14, wherein said genetic lesion or mutation is identified by ascertaining the existence of at least one of: a deletion of one or more nucleotides from a given gene; an addition of one or more nucleotides to a given gene; a substitution of one or more nucleotides of a given gene; a chromosomal rearrangement of a given gene; an alteration in the level of a messenger RNA transcript of a given gene; an aberrant modification of a given gene; the presence of a non-wild type splicing pattern of a messenger RNA transcript of a given gene; a non-wild type level of a protein encoded by a given gene; an allelic loss of a given gene; or an inappropriate post-translational modification of the protein encoded by a given gene.

16. The method of claim 14, wherein said diagnostic test is performed using one or more methods selected from the group consisting of: PCR, RACE PCR, ligation chain reaction, self sustained sequence replication, transcriptional amplification system, Q-Beta replicase, oligonucleotide arrays, mismatch cleavage, single strand conformation polymorphism, denaturing gradient gel electrophoresis, selective oligonucleotide hybridization, selective amplification, selective primer extension, and dynamic allele specific hybridization.

17. The method of claim 14, wherein screening of the subject's genomic DNA sample for detection of genetic lesions or mutations in the genomic DNA sample is carried out to determine if a subject with a lesioned gene is at risk for a disease or disorder characterized by aberrant expression or activity of a given polypeptide.

18. The method of claim 6, wherein performing a diagnosis test on the subject's genomic DNA sample is carried out to determine whether the subject is afflicted with a particular disease or disorder, or is at risk of developing a particular disease or disorder.

19. The method of claim 1, wherein the performing a diagnostic test comprises one or more of: paternity testing, genetic screening, prenatal diagnosis, presymptomatic diagnosis, carrier detection, or forensic chemical analysis.

20. The method of claim 1, wherein the associating the molecular barcode with the biological sample comprises printing a label comprising the barcode and securing the label to a container comprising at least a portion of the sample.

21. The method of claim 1, wherein the molecular barcode is readable using an automated reader.

22. The method of claim 1 further comprising entering the molecular barcode into a searchable database.

23. The method of claim 1, wherein said biological sample is obtained from a human.

24. The method of claim 1, wherein the biological sample is obtained from a biological fluid from one or more of: tissue homogenate, hair, blood, semen, vaginal swab, plasma, serum, ascites, pleural effusion, thoracentesis sample, spinal fluid, lymph fluid, bone marrow, the external sections of the skin, respiratory, intestinal, and genitourinary tracts, stool, urine, sputum, tears, saliva, mixtures of body fluids, vitreous humor, amniotic fluid, chorionic villus samples, blood cells, tumors, organs, tissue, samples of in vitro cell culture constituents, a transudate, an exudate from an abscess, site of infection, or inflammation, and fluid from a normal or diseased joint.

25. The method of claim 1, wherein the biological sample is obtained from an organ, tissue, a biopsy or autopsy specimen, or may comprise primary cells or cultured cells, or may comprise a medium conditioned by any cell, tissue, or organ.

26. The method of claim 1, wherein the linking comprises creating a record in a computer-readable medium, wherein the record comprises the molecular barcode and the diagnostic or prognostic test data.

27. The method of claim 26, wherein said record is a data record in a database configured to allow storage and retrieval thereof.

28. The method of claim 22, wherein the searchable database is stored on a computer readable medium.

29. The method of claim 1, further comprising collecting the biological sample from the mammalian subject, prior to amplifying the DNA in the sample.

30. The method of claim 29, wherein the performing a diagnostic or prognostic test is carried out simultaneously with creating the molecular barcode.

31. The method of claim 6, wherein detecting the presence or absence of the target microorganism in the sample comprises amplifying the DNA of the target microorganism.

32. The method of claim 31, wherein amplifying the DNA of the target microorganism employs a method or combination of methods selected from the group consisting of: variable number tandem repeats analysis, short tandem repeats analysis, complex tandem repeats analysis, restriction fragment length polymorphism analysis, allele specific oligonucleotide analysis, denaturation temperature analysis, single strand conformation polymorphism analysis, amplified fragment length polymorphism analysis, microsatellite or single sequence repeat analysis, rapid amplified polymorphic DNA analysis, sequence tagged site analysis, allele specific polymerase chain reaction analysis, and dynamic allele specific hybridization analysis.

33. The method of claim 31, wherein amplifying the DNA of the sample to generate a molecular barcode and amplifying the DNA of the target microorganism are performed in parallel.

\* \* \* \* \*